US012415082B2

(12) United States Patent
Fishler

(10) Patent No.: US 12,415,082 B2
(45) Date of Patent: Sep. 16, 2025

(54) SYSTEMS AND METHODS FOR USING LEADLESS PACEMAKER TO ASSIST NON-VASCULAR IMPLANTABLE CARDIAC DEFIBRILLATOR

(71) Applicant: Pacesetter, Inc., Sylmar, CA (US)

(72) Inventor: Matthew G. Fishler, Scotts Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 461 days.

(21) Appl. No.: 17/880,928

(22) Filed: Aug. 4, 2022

(65) Prior Publication Data
US 2024/0042220 A1     Feb. 8, 2024

(51) Int. Cl.
*A61N 1/37*     (2006.01)
*A61N 1/372*     (2006.01)
*A61N 1/375*     (2006.01)

(52) U.S. Cl.
CPC ........ *A61N 1/3756* (2013.01); *A61N 1/37211* (2013.01); *A61N 1/37512* (2017.08)

(58) Field of Classification Search
None
See application file for complete search history.

(56) References Cited

U.S. PATENT DOCUMENTS

| | | | |
|---|---|---|---|
| 9,656,091 B2 | 5/2017 | Huelskamp et al. | |
| 2010/0114209 A1* | 5/2010 | Krause | A61N 1/37217 607/32 |
| 2015/0196758 A1 | 7/2015 | Stahmann et al. | |
| 2016/0007873 A1* | 1/2016 | Huelskamp | A61B 5/686 600/510 |
| 2016/0030757 A1 | 2/2016 | Jacobson | |
| 2017/0215731 A1 | 8/2017 | Huelskamp et al. | |
| 2017/0319863 A1 | 11/2017 | Thompson-Nauman et al. | |

(Continued)

OTHER PUBLICATIONS

Extended European Search Report dated Dec. 1, 2023, European Patent Application No. 23183888.9.

(Continued)

*Primary Examiner* — Ankit D Tejani
(74) *Attorney, Agent, or Firm* — Pearl Cohen Zedek Latzer Baratz LLP/Abbott

(57) ABSTRACT

Methods, systems, and devices that detect arrhythmic episodes and perform arrhythmia discrimination are described. Such a system includes a leadless pacemaker (LP) that senses a near-field electrogram (NF-EGM), and a non-vascular implantable cardioverter defibrillator (NV-ICD) that senses a far-field electrogram (FF-EGM). The LP determines cardiac activity information based on the NF-EGM and optionally also based on paced cardiac events caused by the LP. The LP monitors for specific pacemaker condition(s), sends i2i message(s) including the cardiac activity information to the NV-ICD when at least one of the specific pacemaker condition(s) is detected by the LP, and does not send i2i message(s) including the cardiac activity information to the NV-ICD when the LP detects none of the specific pacemaker condition(s) After the NV-ICD receives the i2i message(s) transmitted by the LP, the NV-ICD can detect an arrhythmic episode and/or perform arrhythmia discrimination based on the cardiac activity information included therein.

14 Claims, 7 Drawing Sheets

(56) References Cited

U.S. PATENT DOCUMENTS

2021/0236827 A1    8/2021   Jiang et al.
2021/0402190 A1*  12/2021   Zhang ................... A61B 5/361

OTHER PUBLICATIONS

Response to Invitation pursuant to Rules 70a(1) EPC dated Jun. 17, 2024, European Patent Application No. 23183888.9.
Extended European Search Report dated Feb. 6, 2025, European Patent Application 24215016.7-1122.
U.S. Appl. No. 19/062,363, filed Feb. 25, 2025.

\* cited by examiner

SYSTEMS AND METHODS FOR USING LEADLESS PACEMAKER TO ASSIST NON-VASCULAR IMPLANTABLE CARDIAC DEFIBRILLATOR

FIELD OF TECHNOLOGY

Embodiments described herein generally relate to methods, systems and devices that enable a leadless pacemaker to assist a non-vascular implantable cardiac defibrillator with monitoring for an arrhythmic episode and/or performing arrhythmia discrimination.

BACKGROUND

Conventional implantable cardioverter defibrillators (ICDs) include or are attached to intracardiac electrodes by transvenous leads that are connected to a hermetically sealed container housing the electronics, battery supply and capacitors. Such intracardiac electrodes are also sometimes referred to as intravascular or transvenous electrodes. Conventional ICDs use the intracardiac electrodes to sense intracardiac electrograms (IEGMs) from which cardiac activity, such as ventricular depolarizations and/or atrial depolarizations, can be detected and used to detect arrhythmic episodes and perform arrhythmia discrimination. ICDs are now an established therapy for management of life threatening cardiac arrhythmias, such as ventricular fibrillation (VF) and ventricular tachycardia (VT). While conventional ICDs are very effective at treating VF and VT, the implantation of convention ICDs requires significant surgery and surgical skill, especially regarding lead insertion into the venous system and electrode positioning in the heart.

As ICD therapy becomes more prophylactic in nature and is used in progressively less ill individuals, including children, the requirement of ICD therapy to use transvenous leads and intracardiac electrodes is a major impediment to very long term management, as many individuals will develop complications related to lead system malfunction, fracture or infection. In addition, chronic transvenous lead systems, their removal and reimplantation, can damage major cardiovascular venous systems and the tricuspid valve, as well as result in life threatening perforations of the great vessels and heart. Consequently, use of transvenous lead systems and intracardiac electrodes, despite their many known advantages, are not without their chronic patient management limitations. The problem of lead complications is even greater in children where body growth can substantially alter transvenous lead function and cause additional cardiovascular problems and revisions. Moreover, conventional transvenous ICD systems also increase cost and require specialized interventional rooms and equipment as well as special skill for implantation. These systems are typically implanted by cardiac electrophysiologists who have had a great deal of extra training.

In order to reduce and hopefully eliminated the problems associated with transvenous lead systems and intracardiac electrodes used with conventional ICDs, there has been a concerted effort to transition from using conventional ICDs to using non-vascular ICDs (NV-ICDs), such as sub-cutaneous ICDs (S-ICDs), to treat life threatening cardiac arrhythmias, such as VF and VT. Beneficially, implantation of non-vascular ICDs do not require lead insertion into the venous system and do not require electrode positioning in the heart, and more generally, do not have or are not connected to intracardiac electrodes. Rather, NV-ICDs are able to sense cardiac activity and deliver cardiac therapy using extravascular leads and extracardiac electrodes that are implanted external to the heart and non-vascularly. Typically, an NV-ICD, such as an S-ICD, uses extracardiac electrodes to sense a far-field electrogram (FF-EGM) and detects cardiac activity, such as ventricular depolarizations and/or atrial depolarizations, based on the FF-EGM, and based on the detected cardiac activity detects cardiac arrhythmic episodes and performs arrhythmia discrimination. However, NV-ICDs that rely on FF-EGMs obtained using extracardiac electrodes are more susceptible to under-sensing of cardiac events than conventional ICDs that sense cardiac electrical activity using intracardiac electrodes. Under-sensing of cardiac events during the occurrence of an arrhythmic episode and/or during the performance of arrhythmia discrimination adds risk of inappropriate delivery of or withholding of defibrillation shocks from the NV-ICD. Additionally, NV-ICDs may be more susceptible to noise, such as electromagnetic interference (EMI), electromyogenic, etc., that could result in inappropriate over-sensing of cardiac activity, and thus, in appropriate delivery of cardiac therapy (e.g., an inappropriate defibrillation shock), or the inability to sense intrinsic ventricular activity, and thus, a failure to timely delivery needed cardiac therapy (e.g., a needed defibrillation shock).

SUMMARY

An implantable system according to certain embodiments of the present technology includes a leadless pacemaker (LP) and a non-vascular implantable cardioverter defibrillator (NV-ICD), both of which are implantable in a same patient. The LP comprises two or more electrodes and is configured to be implanted in or on a cardiac chamber of a heart. Additionally, the LP is configured to use at least two of the two or more electrodes to sense a near-field electrogram (NF-EGM) and to selectively pace the cardiac chamber. The NV-ICD comprises two or more extracardiac electrodes configured to be implanted external to the heart. The NV-ICD is configured to use at least two of the two or more extracardiac electrodes to sense a far-field electrogram (FF-EGM). Additionally, the NV-ICD is configured to use at least two of the two or more extracardiac electrodes to selectively deliver a defibrillation shock to the heart. The LP also comprises a transmitter configured to selectively send implant-to-implant (i2i) messages to the NV-ICD, and the NV-ICD also comprises a receiver configured to receive i2i messages from the LP. In certain embodiments the i2i messages are transmitted using conducted communication. In other embodiments, the i2i messages are transmitted using radio frequency (RF) communication.

In accordance with certain embodiments of the present technology, the LP is configured to determine cardiac activity information based on sensed cardiac events detected from the NF-EGM and optionally also based on paced cardiac events caused by the LP performing pacing. The sensed cardiac events can be, e.g., ventricular depolarizations and/or atrial depolarizations, but are not limited thereto. The LP is also configured to monitor for one or more specific pacemaker conditions. In certain embodiments, the LP is configured to send one or more i2i messages including the cardiac activity information to the NV-ICD when at least one of the one or more specific pacemaker conditions is detected by the LP, and not send any i2i messages including the cardiac activity information to the NV-ICD when none of the one or more specific pacemaker conditions is detected by the LP. The NV-ICD is configured to at least one of monitor for an arrhythmic episode or perform arrhythmia discrimination, based on the cardiac activity information obtained from the LP via one or more i2i messages received from the LP. Arrhythmia discrimination, as the term is used herein, refers to one or more of classifying a detected arrhythmic episode as a specific type of arrhythmia (e.g., classifying a detected tachyarrhythmia episode as either VT, AF, or VF), determining that a detected arrhythmic episode has been misclassified, or determining that a detected arrhythmic episode was a false positive detection (e.g., determining that a VT detection was a false positive VT detection).

In certain embodiments the NV-ICD also comprises a transmitter configured to selectively send i2i messages to the LP, and the LP also comprises a receiver configured to receive i2i messages from the NV-ICD. In certain such embodiments, the NV-ICD is configured to selectively send one or more i2i messages to the LP requesting that the LP provide cardiac activity information to the NV-ICD, based upon which the NV-ICD can at least one of monitor for an arrhythmic episode or perform arrhythmia discrimination. In certain such embodiments, one of the one or more specific pacemaker conditions that the LP is configured to monitor for, and in response to which being detected the LP transmits one or more i2i messages including the cardiac activity information to the NV-ICD, comprises the LP receiving the one or more i2i messages from the NV-ICD requesting that the LP provide cardiac activity information to the NV-ICD.

In accordance with certain embodiments, the NV-ICD is configured to normally monitor for an arrhythmic episode and perform arrhythmia discrimination based on cardiac activity detected by the NV-ICD itself from the FF-EGM sensed by the NV-ICD, without using cardiac activity information obtained from the LP. In certain such embodiments, the NV-ICD is configured to at least one of monitor for an arrhythmic episode or perform arrhythmia discrimination based on cardiac activity information obtained from the LP via one or more i2i messages received from the LP, only following (e.g., only within a specified window of time following) the NV-ICD sending the i2i message(s) to the LP requesting that the LP provide cardiac activity information to the NV-ICD.

In accordance with certain embodiments, the NV-ICD is configured to monitor for one or more specific defibrillator conditions, and the NV-ICD is configured to selectively send one or more i2i messages to the LP, requesting that the LP provide cardiac activity information to the NV-ICD, in response to the NV-ICD detecting at least one of the one or more specific defibrillator conditions. In certain such embodiments, one of the one or more specific defibrillator conditions (that the NV-ICD is configured to monitor for, and in response to which being detected the NV-ICD sends one or more i2i messages to the LP requesting that the LP provide cardiac activity information to the NV-ICD), comprises the NV-ICD determining that cardiac activity detected by the NV-ICD from the FF-EGM is likely being at least one of under-sensed or over-sensed. Alternatively, or additionally, one of the one or more specific defibrillator conditions (that the NV-ICD is configured to monitor for and in response to which being detected the NV-ICD sends one or more i2i messages to the LP requesting that the LP provide cardiac activity information to the NV-ICD), comprises the NV-ICD determining that an extracardiac signal is likely preventing the NV-ICD from accurately detecting cardiac activity based on the FF-EGM sensed by the NV-ICD.

In accordance with certain embodiments, the LP is configured to continue sending i2i messages including cardiac activity information to the NV-ICD when at least one of the one or more specific pacemaker conditions continues to be detected, and the LP is configured to stop sending i2i messages including cardiac activity information to the NV-ICD when none of the one or more specific pacemaker conditions continues to be detected.

In accordance with certain embodiments, the LP is configured to determine a rate metric indicative of heart rate or an interval metric indicative of beat-to-beat interval, based on the NF-EGM sensed by the LP. Additionally, the LP is configured to determine when the rate metric exceeds a corresponding rate metric threshold or the interval metric is below a corresponding interval metric threshold.

In accordance with certain embodiments, one of the one or more specific pacemaker conditions (that the LP is configured to monitor for, and in response to which being detected the LP transmits one or more i2i messages including the cardiac activity information to the NV-ICD), comprises the LP determining that the rate metric indicative of heart rate exceeds the corresponding rate metric threshold or the interval metric indicative of beat-to-beat interval is below the corresponding interval metric threshold.

In accordance with certain embodiments, the LP is configured to send one or more i2i messages including cardiac activity information to the NV-ICD each time the LP senses an intrinsic cardiac depolarization and each time the LP delivers a pacing pulse, when the rate metric exceeds the corresponding rate metric threshold or the interval metric is below the corresponding interval metric threshold. In accordance with certain embodiments, the LP is configured to send one or more i2i messages including cardiac activity information to the NV-ICD, less frequently than each time the LP senses an intrinsic cardiac depolarization or delivers a pacing pulse, when the rate metric does not exceed the corresponding rate metric threshold or the interval metric is not below the corresponding interval metric threshold.

In accordance with certain embodiments, the cardiac activity information determined by the LP comprises at least one of the following: a rate metric indicative of heart rate, an interval metric indicative of beat-to-beat interval, an indicator of whether the rate metric indicative of heart rate exceeds a corresponding rate metric threshold, an indicator of whether the rate metric indicative of heart rate is within a corresponding rate metric range, an indicator of whether the interval metric indicative of beat-to-beat interval is below a corresponding interval metric threshold, an indicator of whether the interval metric indicative of beat-to-beat interval is within a corresponding interval metric range, an indicator that a sensed cardiac event occurred, or an indicator that a paced cardiac event occurred. Additional and/or alternative types of cardiac activity information that can be determined by the LP, sent (transmitted) from the LP to the NV-ICD, and used by the NV-ICD to detect an arrhythmic episode and/or perform arrhythmia discrimination. Examples of such additional and/or alternative types of cardiac activity information include information related to morphology of the NF-EGM sensed by the LP, such as, but not limited to, morphological information related to QRS complexes, P-waves, and/or other features of the NF-EGM sensed by the LP. The LP itself can determine whether such features (e.g., QRS complexes) are normal complexes or non-normal complexes and can provide such indications to the NV-ICD. In certain such embodiments, the LP can determine whether such features (e.g., QRS complexes) are classified as a VT complex, a VF complex, etc. The LP can use morphology template matching, wavelet decomposition, and/or the like, to make such determinations. This type of morphological cardiac activity information, that the LP can provide to the NV-ICD, could be very helpful to the NV-ICD, where the NV-ICD is unable to determine such morphological cardiac activity information itself from the FF-EGM sensed by the NV-ICD.

A method, according to certain embodiments of the present technology, is for use by an implantable system including an LP and a NV-ICD, which are both implanted in a same patient. The method includes the NV-ICD sensing an FF-EGM, and the LP sensing a NF-EGM indicative of cardiac electrical activity of a cardiac chamber in or on which the LP is implanted. The method also includes the LP determining cardiac activity information based on the NF-EGM sensed by the LP and/or based on paced cardiac events caused by the LP performing pacing. The method further includes the LP monitoring for one or more specific pacemaker conditions, and the LP transmitting one or more i2i messages including the cardiac activity information to the NV-ICD during a first period of time when at least one of the one or more specific pacemaker conditions is detected by the LP. The method further comprises the NV-ICD receiving the one or more i2i messages transmitted by the LP during the first period of time, and the NV-ICD at least one of monitoring for an arrhythmic episode or performing arrhythmia discrimination, based on the cardiac activity information obtained from the LP via one or more i2i messages received from the LP. The method also comprises the LP not transmitting one or more i2i messages including the cardiac activity information to the NV-ICD during a second period of time when none of the one or more specific pacemaker conditions is detected by the LP.

In accordance with certain embodiments of the present technology, the method comprises the NV-ICD selectively sending one or more i2i messages to the LP requesting that the LP provide cardiac activity information to the NV-ICD, based upon which the NV-ICD can at least one of monitor for an arrhythmic episode or perform arrhythmia discrimination. In certain such embodiments, one of the one or more specific pacemaker conditions that the LP monitors for (and in response to which being detected the LP transmits one or more i2i messages including the cardiac activity information to the NV-ICD), comprises the LP receiving the one or more i2i messages from the NV-ICD requesting that the LP provide cardiac activity information to the NV-ICD.

In accordance with certain embodiments of the present technology, the method includes the NV-ICD normally monitoring for an arrhythmic episode and performing arrhythmia discrimination based on cardiac activity detected by the NV-ICD itself from the FF-EGM sensed by the NV-ICD, without using cardiac activity information obtained from the LP. The method also includes the NV-ICD at least one of monitoring for an arrhythmic episode or performing arrhythmia discrimination based on cardiac activity information obtained from the LP via one or more i2i messages received from the LP, only following the NV-ICD sending the i2i message(s) to the LP requesting that the LP provide cardiac activity information to the NV-ICD.

In accordance with certain embodiments of the present technology, the method further comprises the NV-ICD monitoring for one or more specific defibrillator conditions, and the NV-ICD sending one or more i2i messages to the LP, requesting that the LP provide cardiac activity information to the NV-ICD, in response to the NV-ICD detecting at least one of the one or more specific defibrillator conditions. In accordance with certain such embodiments, one of the one or more specific defibrillator conditions that the NV-ICD monitors for (and in response to which being detected the NV-ICD sends one or more i2i messages to the LP requesting that the LP provide cardiac activity information to the NV-ICD), comprises the NV-ICD determining that cardiac activity detected by the NV-ICD from the FF-EGM is likely being at least one of under-sensed or over-sensed. Alternatively, or additionally, one of the one or more specific defibrillator conditions (that the NV-ICD monitors for and in response to which being detected the NV-ICD sends one or more i2i messages to the LP requesting that the LP provide cardiac activity information to the NV-ICD), comprises the NV-ICD determining that an extracardiac signal is likely preventing the NV-ICD from accurately detecting cardiac activity based on the FF-EGM sensed by the NV-ICD.

In accordance with certain embodiments of the present technology, the method comprises the LP continuing sending i2i messages including cardiac activity information to the NV-ICD when at least one of the one or more specific pacemaker conditions continues to be detected, and the LP stopping sending i2i messages including cardiac activity information to the NV-ICD when none of the one or more specific pacemaker conditions continues to be detected.

In accordance with certain embodiments of the present technology, the method includes the LP determining a rate metric indicative of heart rate or an interval metric indicative of beat-to-beat interval, based on the NF-EGM sensed by the LP. The method also includes the LP determining when the rate metric exceeds a corresponding rate metric threshold or the interval metric is below a corresponding interval metric threshold.

In accordance with certain embodiments of the present technology, one of the one or more specific pacemaker conditions that the LP monitors for (and in response to which being detected the LP transmits one or more i2i messages including the cardiac activity information to the NV-ICD), comprises the LP determining that the rate metric indicative of heart rate exceeds the corresponding rate metric threshold or the interval metric indicative of beat-to-beat interval is below the corresponding interval metric threshold.

In accordance with certain embodiments of the present technology, the method further comprises the LP sending one or more i2i messages including cardiac activity information to the NV-ICD each time the LP senses an intrinsic cardiac depolarization and each time the LP delivers a pacing pulse, when the rate metric exceeds the corresponding rate metric threshold or the interval metric is below the corresponding interval metric threshold.

In accordance with certain embodiments of the present technology, the method further comprises the LP sending one or more i2i messages including cardiac activity information to the NV-ICD, less frequently than each time the LP senses an intrinsic cardiac depolarization or delivers a pacing pulse, when the rate metric does not exceed the corresponding rate metric threshold or the interval metric is not below the corresponding interval metric threshold.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology relate to methods, systems and devices whereby a leadless pacemaker (LP) assists a non-vascular implantable cardiac defibrillator (NV-ICD) with monitoring for an arrhythmic episode and/or performing arrhythmia discrimination. Arrhythmia discrimination, as the term is used herein, refers to one or more of classifying a detected arrhythmic episode as a specific type of arrhythmia, e.g., classifying a detected tachyarrhythmia episode as either VT, atrial fibrillation (AF), or VF, determining that a detected arrhythmic episode has been misclassified, or determining that a detected arrhythmic episode was a false positive detection, e.g., a VT detection was a false positive VT detection. Before providing additional details of the specific embodiments of the present technology mentioned above, an example environment in which embodiments of the present technology can be useful will first be described with reference to FIGS. 1-3. More specifically, FIGS. 1-3 will be used to describe an example cardiac therapy system, wherein cardiac therapy can be performed by multiple medical devices, which may include one or more leadless cardiac pacemakers and a NV-ICD. A leadless cardiac pacemaker can also be referred to more succinctly herein as a leadless pacemaker (LP).

Figure 1:
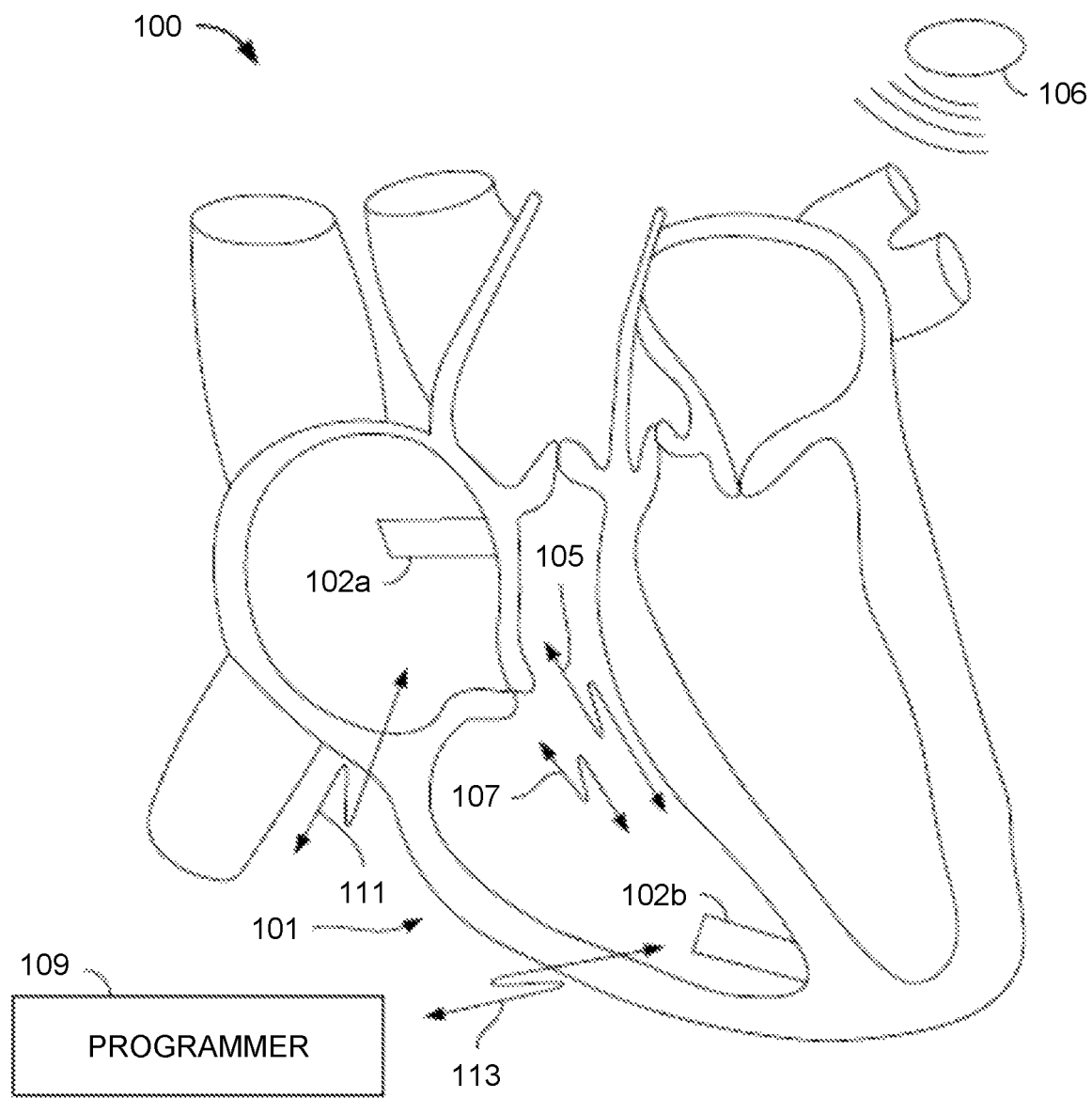
FIG. 1 illustrates a system that includes a plurality of implantable devices that are implanted in a patient and an external programmer that can be used to program and/otherwise communicate with the implantable devices.

FIG. 1 illustrates a system 100 that is configured to be implanted in a heart 101. The system 100 includes LPs 102a and 102b located in different chambers of the heart 101. LP 102a is located in a right atrium, while LP 102b is located in a right ventricle. LPs 102a and 102b can communicate with one another to inform one another of various local physiologic activities, such as local intrinsic events, local paced events, and/or the like. LPs 102a and 102b may be constructed in a similar manner, but operate differently based upon which chamber LP 102a or 102b is located. The LPs 102a and 102b may sometimes be referred to collectively herein as the LPs 102, or individually as an LP 102.

In certain embodiments, LPs 102a and 102b communicate with one another, and/or with an NV-ICD 106, by conductive communication through the same electrodes that are used for sensing and/or delivery of pacing therapy. The LPs 102a and 102b may also be able to use conductive communication to communicate with a non-implanted device, e.g., an external programmer 109, having electrodes placed on the skin of a patient within which the LPs 102a and 102b are implanted. While not shown (and not preferred, since it would increase the size and power consumption of the LPs 102a and 102b), the LPs 102a and 102b can potentially include an antenna and/or telemetry coil that would enable them to communicate with one another, the NV-ICD 106 and/or a non-implanted device using RF or inductive communication. While only two LPs are shown in FIG. 1, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber. It is also possible that a single LP be implanted within a patient, e.g., in or on the RV chamber, the RA chamber, or the LV chamber, but not limited thereto.

In some embodiments, one or more LP 102a, 102b can be co-implanted with the NV-ICD 106. Each LP 102a, 102b uses two or more electrodes located within, on, or within a few centimeters of the housing of the pacemaker, for pacing and sensing at the cardiac chamber, for bidirectional conductive communication with one another, with an external programmer 109, and/or the NV-ICD 106. The NV-ICD 106 can be intended for non-vascular (e.g., subcutaneous) implantation at a site near the heart 101. The NV-ICD 106 can include or be attached by a lead (not shown in FIG. 1) to one or more extracardiac electrodes (not shown in FIG. 1) that provide for detection of far-field EGM signals and for selective delivery of cardiac therapy (e.g., a defibrillation shock). The extracardiac electrodes of or attached to the NV-ICD 106 can also be used for conductive communication with one or more other implanted devices, such as the LP(s) 102a and/or 102b and/or with the programmer 109. It is also possible that the NV-ICD 106 can also include an antenna that is configured to wirelessly communicate with an external device, such as the external programmer 109, in accordance with one or more wireless communication protocols (e.g., Bluetooth, Bluetooth low energy, Wi-Fi, etc.).

Figure 2:
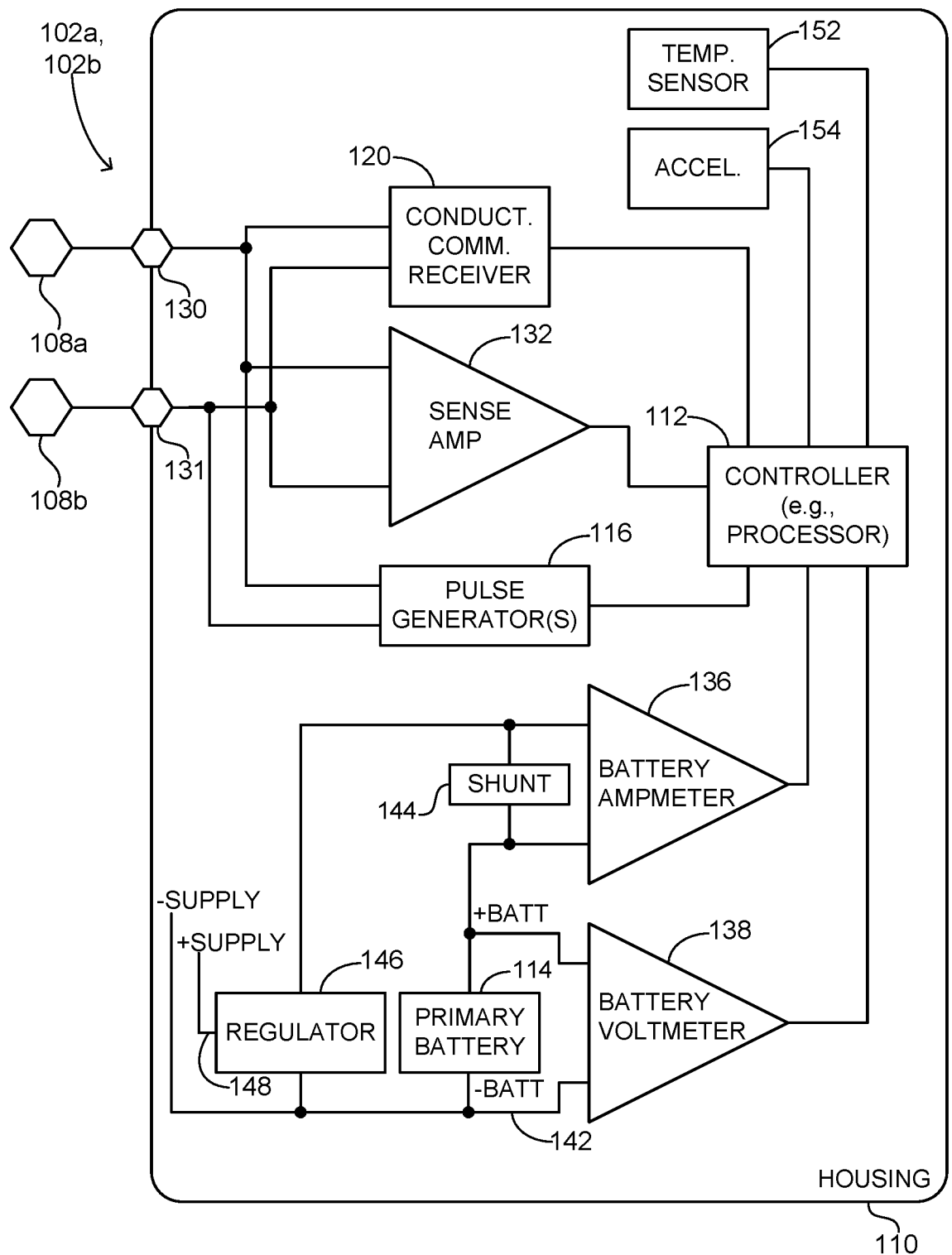
FIG. 2 is a block diagram of a single LP in accordance with certain embodiments herein.

Referring to FIG. 2, a block diagram shows an example embodiment for portions of the electronics within LPs 102a, 102b configured to provide conductive communication through the same electrodes that are used for cardiac pacing and/or sensing. Each of the LPs 102a, 102b includes at least two leadless electrodes configured for delivering cardiac pacing pulses, sensing evoked and/or natural cardiac electrical signals, and uni-directional and/or bi-directional communication. In FIG. 2 (and FIG. 3) the two electrodes shown therein are labeled 108a and 108b. Such electrodes can be referred to collectively as the electrodes 108, or individually as an electrode 108. An LP 102, or other type of IMD, can include more than two electrodes, depending upon implementation.

In FIG. 2, each of the LPs 102a, 102b is shown as including a conductive communication receiver 120 that is coupled to the electrodes 108 and configured to receive conductive communication signals from the other LP, 102 the NV-ICD 106, and/or the external programmer 109, but not limited thereto. Although one conductive communication receiver 120 is depicted in FIG. 2, in other embodiments, each LP 102a, 102b may only include one or more additional receivers. As will be described in additional detail below, a pulse generator 116 can function as a transmitter that transmits conductive communication signals using the electrodes 108. In certain embodiments, LPs 102a and 102b may communicate over more than just first and second communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses. Usage of the electrodes 108 for communication enables the one or more LPs 102a, 102b to perform antenna-less and telemetry coil-less communication. Where two implantable devices (such as two LPs 102a and 102b) communicate with one another using conductive communication, such conductive communication can be referred to as implant-to-implant (i2i) communication. Messages that are transmitted between implantable devices, such as between the LPs 102a and 102b, or between one of the LPs 102 and the NV-ICD 106, can be referred to herein as i2i messages. Such i2i messages can be transmitted using conductive communication, or alternatively, using RF communication or inductive communication. It is noted that the term "transmit" and the term "send" are used interchangeably herein. Similarly, the term "transmitted" and the term "sent" are used interchangeably herein.

Optionally, the LP (or other IMD) that receives any conductive communication signal from another LP (or other IMD) or from a non-implanted device (e.g., a programmer 109) may transmit a receive acknowledgement indicating that the receiving LP (or other IMD, or non-implanted device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. Other variations are also possible and within the scope of the embodiments described herein. Each conductive communication signal can include one or more sequences of conductive communication pulses. In accordance with certain embodiments, conductive communication pulses are delivered during cardiac refractory periods that are identified or detected by the LP(s) and/or other IMD(s). In accordance with certain embodiments, conductive communication pulses are sub-threshold, i.e., they are below the capture threshold for the patient.

Event messages transmitted between the LPs enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously.

For synchronous event signaling, LPs 102a and 102b may maintain synchronization and regularly communicate at a specific interval. Synchronous event signaling allows the transmitter and receivers in each LP 102a, 102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 μs, where the Tx/Rx time slots occur periodically (e.g., every 10-20 ms). Such time slots can also be referred to as windows.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

Still referring to FIG. 2, each LP 102a, 102b is shown as including a controller 112 and one or more pulse generator(s) 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and a pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer 109 may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse-width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 μA. The same LP 102a, 102b may implement an event message utilizing event signaling parameters for amplitude, pulse-width, pulse rate, etc. that correspond to a current draw of approximately 0.5 µA for transmit. LP 102a, 102b may combine the event message transmissions with pacing pulses. For example, LP 102a, 102b may use a 50 µs wakeup transmit pulse having an amplitude of 2.5V which would draw 250 nC (nano Coulombs) for an electrode load of 500 ohm.

In some embodiments, the individual LP 102a can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP is communicating, the conductive communication may be unidirectional or bidirectional.

FIG. 2 depicts a single LP 102a (or 102b) and shows the LP's functional elements substantially enclosed in a hermetic housing 110. The LP 102a (or 102b) has at least two electrodes 108 located within, on, or near the housing 110, for delivering pacing pulses to and sensing electrical activity from the muscle of the cardiac chamber, and for conductive communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted NV-ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more LPs and/or the NV-ICD 106 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to an external programmer. Similarly, information communicated on the outgoing channel can also include a message to another LP and/or the NV-ICD, that the sending leadless cardiac pacemaker has sensed a heartbeat or has delivered a pacing pulse at the location of the sending pacemaker.

Referring again to FIGS. 1 and 2, the system 100 may comprise the NV-ICD 106 in addition to one or more LPs 102a, 102b configured for implantation in electrical contact with a cardiac chamber and for performing cardiac rhythm management functions. The implantable NV-ICD 106 and the one or more LPs 102a, 102b can configured for leadless intercommunication by information conduction through body tissue and/or wireless transmission between transmitters and receivers in accordance with certain embodiments discussed herein. As shown in the illustrative embodiments, each LP 102a, 102b can comprise two or more leadless electrodes 108 configured for delivering cardiac pacing pulses, sensing evoked and/or natural cardiac electrical signals, and bidirectionally communicating with one another and/or the co-implanted NV-ICD 106.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the LP 102. The shunt 144 enables the battery current monitor 136 to provide the controller 112 with an indication of battery current drain and indirectly of device health. The illustrative power supply can be the primary battery 114.

Referring to FIG. 2, the LP is shown as including a temperature sensor 152. The temperature sensor 152 can be any one of various different types of well-known temperature sensors, or can be a future developed temperature sensor. The temperature sensor 152 can be used in various manners. For example, the temperature sensor 152 can be used to detect an activity level of the patient to adjust a pacing rate, i.e., for use in rate responsive pacing. Accordingly, the controller 112 can be configured to detect an activity level of a patient based on core blood temperature measurements obtained using the temperature sensor 152.

Referring to FIG. 2, the LP is also shown as including an accelerometer 154 which can be hermetically contained within the housing 110. The accelerometer 154 can be any one of various different types of well-known accelerometers, or can be a future developed accelerometer. The accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an (electrogram) EGM sensed using the electrodes 108, and/or sensed using a plethysmography signal obtained using a plethysmography sensor (not shown) or a heart sound sensor (e.g., provided by the accelerometer 154), but is not limited thereto.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
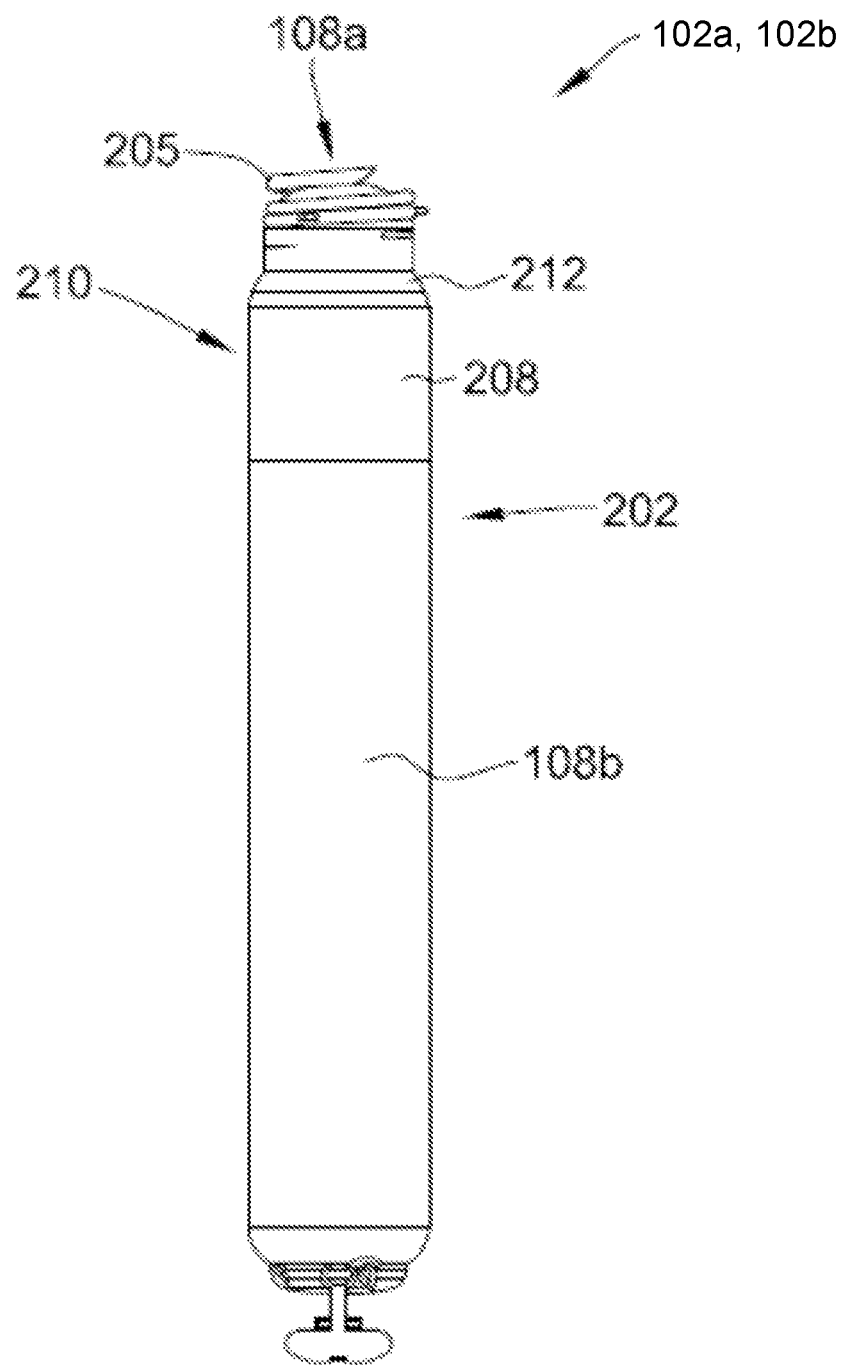
FIG. 3 illustrates an LP in accordance with certain embodiments herein.

FIG. 3 shows an example form factor of an LP 102a, 102b. The LP can include a hermetic housing 202 (110) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2.

The housing can also include an electronics compartment 210 within the housing that contains the electronic components necessary for operation of the pacemaker, including, e.g., a pulse generator, a receiver, a battery, and a processor for operation. The hermetic housing 202 can be adapted to be implanted on or in a human heart, and can be cylindrically shaped, rectangular, spherical, or any other appropriate shapes, for example. The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate electrodes 108a and 108b. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 4:
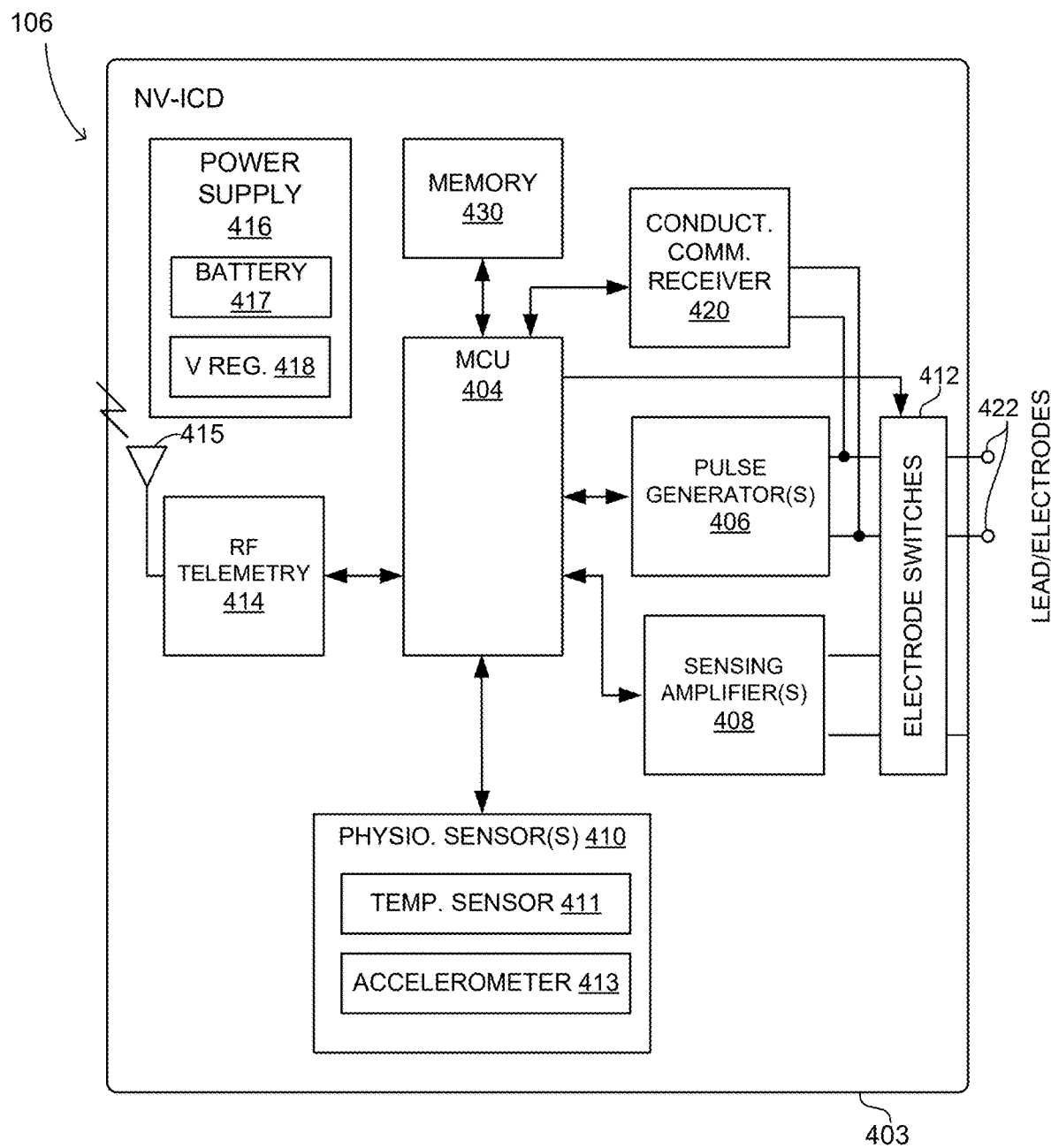
FIG. 4 is a block diagram of an NV-ICD in accordance with certain embodiments herein.

The high level block diagram in FIG. 4 will now be used to describe an example implementation of the NV-ICD 106 introduced above in the discussion of FIG. 1. The NV-ICD 106 is shown as including a microcontroller unit (MCU) 404, one or more pulse generator(s) 406, one or more sensing amplifier(s) 408, one or more physiologic sensor(s) 410, electrode switches 412, electrodes 422, an optional RF telemetry circuit 414, a power supply 416, and memory 430.

The NV-ICD 106 is also shown as including a conductive communication receiver 420 that is coupled to the electrodes 422 and configured to receive conductive communication signals from at least one LP 102a and/or 102b, and/or the external programmer 109, but not limited thereto. Although one conductive communication receiver 420 is depicted in FIG. 4, in other embodiments, each NV-ICD 106 can include one or more additional conductive communication receivers. A pulse generator 406 can function as a transmitter that transmits conductive communication signals using the electrodes 422, which are extracardiac electrodes. Such extracardiac electrode 422 can be coupled to one or more extravascular leads, which is/are not specifically shown.

As is well known in the art, the MCU 404 (also referred to herein as a control unit or controller) typically includes a microprocessor, or equivalent control circuitry, designed specifically for controlling the delivery of stimulation therapy (if the SID is an IDC) and may further include RAM or ROM memory, logic and timing circuitry, state machine circuitry, and I/O circuitry. Typically, the MCU 404 includes the ability to process or monitor input signals (data) as controlled by a program code stored in a designated block of memory. The details of the design and operation of the MCU 404 are not critical to the technology. Rather, any suitable MCU 404 that includes at least one processor may be used that carries out the functions described herein. The use of microprocessor-based control circuits for performing timing and data analysis functions are well known in the art. The MCU 404 can control the delivery of defibrillation shocks, as well as the monitoring of various types of physiologic measures.

The pulse generator(s) 406 can generate pulses that are provided to the electrodes 422 for performing conductive communication. The pulse generator(s) 406 can generate pulses for stimulating patient tissue. The electrodes 422 can be included on one or more leads, and/or can be located on or adjacent to a housing 403 of the NV-ICD 106. Where more than two electrodes are available for delivering stimulation, the electrode switches 412 can be used to select specific combinations of electrodes under the control of the MCU 404. The pulse generator(s) 406 are controlled by the MCU 404 via appropriate control signals to trigger or inhibit the generation of pulses. Depending upon the implementation, the various components of the MCU 404 may be implemented as separate software modules or the modules may be combined to permit a single module to perform multiple functions. In addition, although described as being components of the MCU 404, some or all of the above discussed modules may be implemented separately from the MCU 404, e.g., using one or more application specific integrated circuits (ASICs), field programmable gate arrays (FPGAs), or the like.

The electrode switches 412, which can also be referred to as switching circuitry 412, includes a plurality of switches for connecting the desired electrodes to the appropriate I/O circuits, thereby providing complete electrode programmability. Accordingly, the switching circuitry 412, in response to a control signal from the MCU 404, determines the polarity of the stimulation pulses (e.g., unipolar, bipolar, combipolar, etc.) by selectively closing the appropriate combination of switches (not shown) as is known in the art. The switching circuitry 412 can also switch among the various different combinations of electrodes. The switching circuitry 412 determines the "sensing polarity" of the cardiac signal by selectively closing the appropriate switches, as is also known in the art. In this way, a clinician may program the sensing polarity independent of the stimulation polarity. In certain embodiments, where there are only two electrodes, the switching circuitry 412 can be eliminated.

The sensing amplifier(s) 408 can include, e.g., atrial and/or ventricular sensing amplifiers that are selectively coupled to various combinations of electrodes to provide for various different sensing vectors that can be used, e.g., for detecting the presence of cardiac activity in one or more of the four chambers of the heart. Accordingly, the sensing amplifier(s) 408 can include dedicated sense amplifiers, multiplexed amplifiers or shared amplifiers. The sensing amplifier(s) 408 can also be used to sense conductive communication pulses, or more generally conductive communication signals, that originate from an LP (e.g., 102a or 102b). Each sensing amplifier 408 can employ one or more low power, precision amplifiers with programmable gain and/or automatic gain control, bandpass filtering, and a threshold detection circuit, as known in the art, to selectively sense the signal of interest, which as noted above, can be a cardiac signal and/or a conductive communication signal. The automatic gain control enables the NV-ICD 106 to deal effectively with the difficult problem of sensing the low amplitude signal characteristics of atrial or ventricular fibrillation. The outputs of the sensing amplifier(s) 408 are connected to the MCU 404. At least a pair of the extracardiac electrodes 422 (one of which can be provided by a conductive housing of the NV-ICD) and at least one of the sensing amplifier(s) 408 can be used to sense a far-field EGM (FF-EGM).

Although not specifically shown in FIG. 4, cardiac signals can also be applied to the inputs of an analog-to-digital (ND) data acquisition system that is configured to acquire intracardiac electrogram signals, convert the raw analog data into a digital signal, and store the digital signals for later processing and/or telemetric transmission to an external programmer or a bedside monitor or personal advisory module (PAM). The data acquisition system can be coupled to various leads and/or electrodes through the switching circuitry 412 to sample cardiac signals (e.g., an FF-EGM) across any pair of desired electrodes. The MCU 404 is further coupled to the memory 430 by a suitable data/address bus, or the like, wherein the programmable operating parameters used by the MCU 404 are stored and modified, as required, in order to customize the operation of NV-ICD 106 to suit the needs of a particular patient. Such operating parameters can define, for example, a waveshape and vector of each shocking pulse to be delivered to the patient's heart within each respective tier of therapy.

The operating parameters of the NV-ICD 106 may be non-invasively programmed into the memory 430 through an RF telemetry circuit 414 in telemetric communication with an external device or bedside monitor. The RF telemetry circuit 414, which can also be referred to as an RF communication subsystem or an RF transceiver 414, is activated by the MCU 404 by a control signal. The RF telemetry circuit 414 enables the NV-ICD 106 to wirelessly communicate with an external device using RF communication signals that are transmitted and received via an antenna 415. The RF telemetry circuit 414, which is communicatively coupled to the MCU 404, can be a Bluetooth Low Energy (BLE) radio, or some other RF communication subsystem, and may be implemented as an RF integrated circuit (IC). The remaining set of circuits or subsystems of the NV-ICD 106 shown in FIG. 4, or just a subset thereof, can be implemented in a custom application specific IC (ASIC), which can also be referred to as a custom chip. In other words, the terms IC and chip are used interchangeably herein. The RF telemetry circuit 414 can allow one or more FF-EGMs and status information relating to the operation of the NV-ICD 106 (as contained in the MCU 404 or memory 430) to be sent to an external device through an established RF communication link. An internal warning device, not specifically shown, may be provided for generating perceptible warning signals to the patient via vibration, voltage or other methods.

Alternatively, or additionally, the operating parameters of the NV-ICD 106 may be non-invasively programmed into the memory 430 through the conductive communication receiver 420 that is configured to received conductive communication signals from an external device or bedside monitor. As noted above, a pulse generator 406, under control of the MCU 404, can be used to transmit conductive communication signals from the NV-ICD 106 to an external device or bedside monitor, wherein such an external device can be the external programmer 109. It would also be possible for the RF telemetry circuit 414 to be eliminated, if the NV-ICD 106 relied solely on conductive communications to communicate with an external programmer 109 and/or other implantable devices.

The memory 430 may include instructions operable to cause the MCU 404 to perform the methods, or portions thereof, described herein. In one embodiment, the memory 430 may comprise a non-volatile, non-transitory computer readable medium and/or volatile memory containing such instructions. Alternatively, the MCU 404 may include an internal computer readable medium or memory including the instructions.

The physiologic sensors 410 can include a temperature sensor 411, an accelerometer 413, and/or other types of physiologic sensors. The physiological sensor(s) 410 may further be used to detect changes in cardiac output, changes in the physiological condition of the heart, or diurnal changes in activity, or the like. While shown as being included within the NV-ICD 106, it is to be understood that one or more of the physiologic sensor(s) 410 may also be external to the NV-ICD 106, yet still be implanted within or carried by the patient. Other types of physiologic sensors are also known, for example, sensors that sense the oxygen content of blood, respiration rate and/or minute ventilation, pH of blood, ventricular gradient, stroke volume, cardiac output, contractility, etc.

The power supply 416, which can include a battery 417 and a voltage regulator 418, provides operating power to all of the circuits or subsystem shown in FIG. 4. The specific type of battery 417 included in the NV-ICD 106 can vary depending on the capabilities of NV-ICD 106. The battery 417 should be capable of operating at low current drains for long periods, and then be capable of providing high-current pulses (for capacitor charging) when the patient requires a shock pulse. The battery 417 should also have a predictable discharge characteristic so that elective replacement time can be detected. Accordingly, appropriate batteries are employed. One or more voltage regulators 418 can step up or step down a voltage provide by the battery 417 to produce one or more predetermined voltages useful for powering the various circuits or subsystems of the NV-ICD 106.

The NV-ICD 106 can include additional and/or alternative types of circuits or subsystems, not specifically shown in FIG. 4. For example, the NV-ICD 106 can also include an impedance measurement circuit that can be used, e.g., for measuring respiration or minute ventilation; measuring thoracic impedance for determining shock thresholds; detecting when the device has been implanted; measuring respiration; and detecting the opening of heart valves, etc. Such an impedance measurement circuit can be coupled to the switching circuitry 412 so that any desired combination of electrodes 822 may be used for measuring impedance.

The NV-ICD 106 can sense cardiac activity and deliver cardiac therapy using extravascular leads and the extracardiac electrodes 422 that are implanted external to the heart and non-vascularly. For example, the NV-ICD 106 can use extracardiac electrodes 422 to sense a FF-EGM and can detect cardiac activity, such as ventricular depolarizations and/or atrial depolarizations, based on the FF-EGM. The NV-ICD 106 can detect cardiac arrhythmic episodes and perform arrhythmia discrimination based on the cardiac activity that is detected based on the sensed FF-EGM. However, because the NV-ICD 106 relies on FF-EGMs obtained using extracardiac electrodes 422, such EGMs are more susceptible to under-sensing of cardiac events than IEGMs sensed by conventional ICDs that sense cardiac electrical activity using intracardiac electrodes. As noted above, under-sensing of cardiac events during the occurrence of an arrhythmic episode and/or during the performance of arrhythmia discrimination adds risk of inappropriate delivery of or withholding of defibrillation shocks from the NV-ICD. Additionally, the FF-EGMs may be more susceptible to noise, such as electromagnetic interference (EMI), electromyogenic, etc., that could result in inappropriate over-sensing of cardiac activity, and thus, inappropriate delivery of cardiac therapy (e.g., an inappropriate defibrillation shock), or the inability to sense intrinsic ventricular activity, and thus, a failure to timely deliver needed cardiac therapy (e.g., a needed defibrillation shock). Certain features of the present technology, which are described below, are used to overcome all or some of the above described deficiencies associated with the NV-ICD 106 relying on FF-EGMs to detect arrhythmic episodes and perform arrhythmia discrimination. More specifically, in accordance with certain embodiments of the present technology, cardiac events detected by a ventricular LP are used to supplement the capabilities of the NV-ICD 106, to reduce the probability of the NV-ICD 106 inappropriately delivering cardiac therapy (e.g., an inappropriate defibrillation shock) due to inappropriate over-sensing of cardiac activity, as well as to reduce the probability of the NV-ICD 106 failing to timely delivery needed cardiac therapy (e.g., a needed defibrillation shock) due to inappropriate under-sensing of cardiac activity.

In accordance with certain embodiments of the present technology, an NV-ICD (e.g., 106) uses cardiac activity information received from an LP (e.g., 102b) implanted in (or on) a cardiac chamber (e.g., a ventricular chamber) to supplement and/or replace cardiac activity detected by the NV-ICD itself, in order to improve the ability of the NV-ICD to accurately detect arrhythmic episodes and/or perform arrhythmia discrimination. The LP that is implanted in (or on) a cardiac chamber can be, e.g., the LP 102b in FIG. 1, which is implanted in the right ventricular chamber of the heart. Alternatively, such an LP can instead be implanted in or on the left ventricular chamber of the heart. It would also be possible that the LP that provides cardiac activity information to the NV-ICD is implanted in an atrial chamber, such as the LP 102a implanted in the right atrial chamber. However, it is preferred that the LP that provides cardiac information to the NV-ICD be implanted in or on a ventricular chamber, most preferably the right ventricular chamber. Where an LP is implanted in or on a ventricular chamber, the LP can be referred to as a ventricular LP, or more succinctly as a vLP. Where an LP is implanted in or on an atrial chamber, the LP can be referred to as an atrial LP, or more succinctly as an aLP.

As will be described in further detail below, there are various different ways in which an LP can provide supplemental information, and more specifically cardiac activity information determined by the LP, to an NV-ICD. In certain embodiments, an LP provides supplemental information to an NV-ICD in response to receiving an on-demand request from the NV-ICD. In such embodiments, the NV-ICD transmits a request to an LP via one or more i2i messages for the LP to actively reply with cardiac activity information determined by the LP. In such an embodiment, there may normally be no interaction or communication between the NV-ICD and the LP. However, the NV-ICD may purposefully contact the LP via one or more i2i messages to request a response from the LP that includes cardiac activity information determined by the LP.

In certain such embodiments, the NV-ICD may send one or more i2i messages to the LP, requesting cardiac activity information from the LP, when the NV-ICD loses robust sensing of an FF-EGM. Alternatively, or additionally, the NV-ICD may send one or more i2i messages to the LP, requesting cardiac activity information from the LP, when the NV-ICD suspects extracardiac signals are disrupting the ability of the NV-ICD to accurately sense cardiac activity from the FF-EGM sensed by the NV-ICD. Other variations are also possible and within the scope of the embodiments described herein. Additional details of how and when an LP can provide supplemental information to an NV-ICD, in response to an on-demand request received from the NV-ICD, are described below with reference to the flow diagram of FIG. 5B.

In certain other embodiments, an LP can provide on-demand transmissions of cardiac activity information to an NV-ICD when deemed necessary or appropriate by the LP, without receiving a request from the NV-ICD. For example, an LP can provide on-demand transmissions of cardiac activity information when a rate metric (indicative of HR) determined by the LP exceeds a specified rate metric threshold, or when an interval metric (indicative of a beat-to-beat interval, e.g., R-R interval or P-P interval) determined by the LP falls below a specified interval metric threshold, but is not limited thereto. In such embodiments, there may be normally no interaction or communication between the NV-ICD and the LP. However, when the LP determines that the rate metric exceeds the specified rate metric threshold, or the interval metric falls below the specified interval metric threshold, the LP automatically initiates transmission of one or more i2i messages that includes cardiac activity information to the NV-ICD. Thereafter, when the rate metric no longer exceeds the specified rate metric threshold, or the interval metric no longer falls below the specified interval metric threshold, the LP automatically stops the transmission of the cardiac activity information to the NV-ICD. Additional details of how and when an LP can decide on its own to provide supplemental information to an NV-ICD, are described below with reference to the flow diagram of FIG. 5C.

In still other embodiments, an LP can frequently (e.g., once per cardiac cycle) transmit cardiac activity information to an NV-ICD, and more specifically, the LP can inform the NV-ICD of each cardiac event sensed by the LP and each cardiac event paced by the LP. Alternatively, the frequency at which the LP transmits cardiac information to the NV-ICD can depend on a rate metric or an interval metric determined by the LP. For example, when the LP determines that a rate metric does not exceed a specified rate metric threshold, or an interval metric does not fall below a specified interval metric threshold, the LP transmits cardiac activity information to the NV-ICD periodically, e.g., once every Nth paced/sensed event, where N>1; and when the LP determines that the rate metric exceeds the specified rate metric threshold, or the interval metric falls below the specified interval metric threshold, the LP transmits cardiac activity information to the NV-ICD more frequently, e.g., once every Mth paced/sensed event, where 1≤M<N.

Figure 5A:
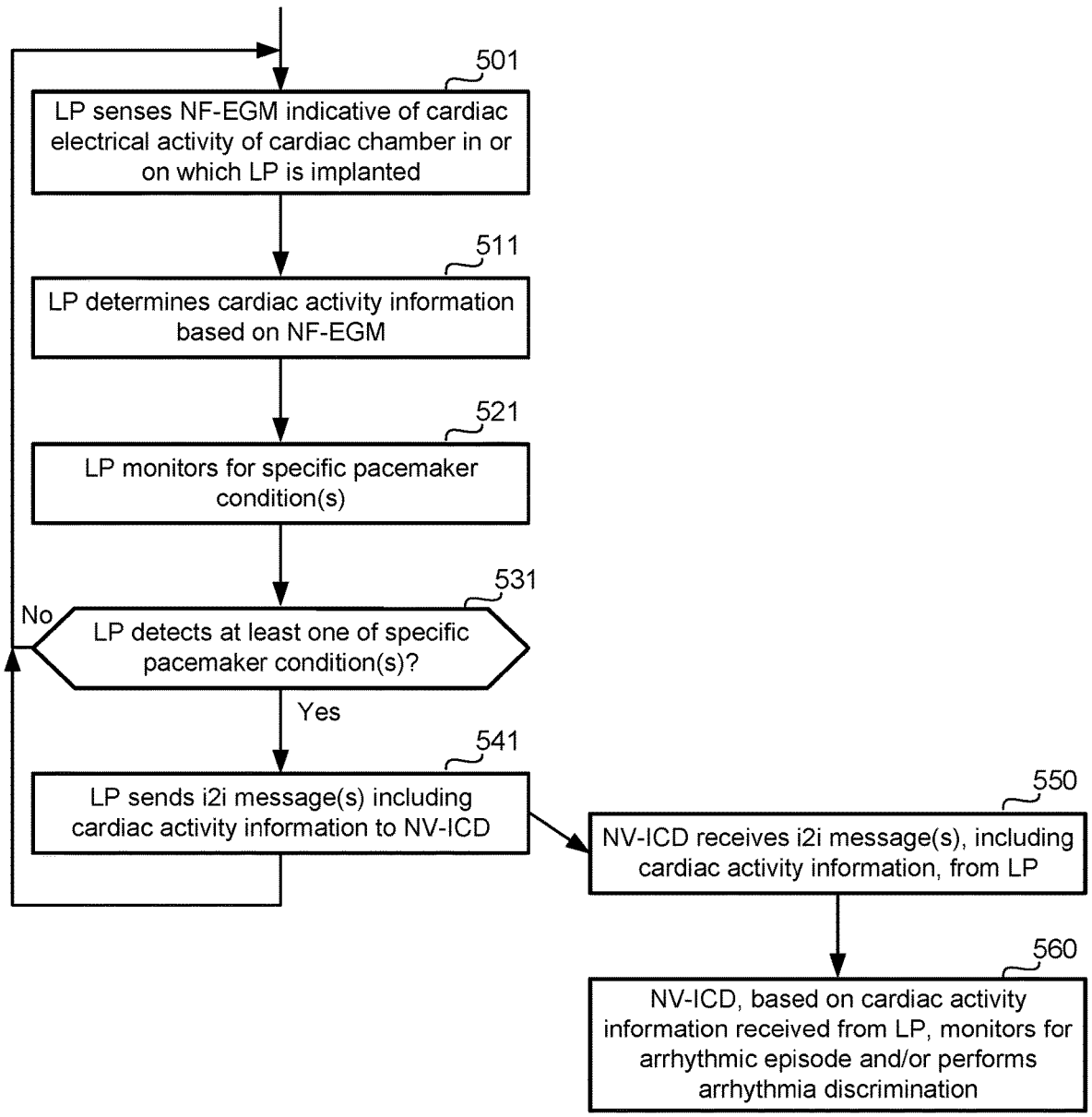
FIG. 5A is a high level flow diagram that is used to describe certain embodiments of the present technology wherein an LP selectively sends cardiac activity information to an NV-ICD.

The high level flow diagram of FIG. 5A will initially be used to describe methods according to various embodiments of the present invention, which were introduced above, wherein such methods are for use by an implantable system including an LP and an NV-ICD. Example details of such an LP (e.g., 102b) and an NV-ICD (e.g., 106) were described above with reference to FIGS. 1-4. However, it should be noted that the methods described below are not limited to use with the specific LPs and NV-ICDs described herein. Such an LP can include two or more electrodes (e.g., 108a, 108b) and be configured to be implanted in or on a cardiac chamber of a heart. Further, the LP can be configured to use at least two of the two or more electrodes to sense a near-field electrogram (NF-EGM) and to selectively pace the cardiac chamber. The NV-ICD can include two or more extracardiac electrodes configured to be implanted external to the heart. Further, the NV-ICD can be configured to use at least two of the two or more extracardiac electrodes (e.g., 422) to sense a far-field electrogram (FF-EGM). Additionally, the NV-ICD can be configured to use at least two of the two or more extracardiac electrodes (e.g., 422) to selectively deliver a defibrillation shock to the heart. In FIG. 5A, as well as FIGS. 5B-5C, the steps shown on the left are performed by the LP (e.g., 102b) and the steps shown on the right are performed by the NV-ICD (e.g., 106).

Referring to FIG. 5A, step 501 involves the LP sensing a near-field electrogram (NF-EGM) indicative of cardiac electrical activity of a cardiac chamber in or on which the LP is implanted. For an example, referring briefly back to FIGS. 1-3, an LP 102 can sense the NF-EGM using the electrodes 108a, 108b and the sense amplifier 132. As noted above, the LP that performs step 501 can be implanted in or on a ventricular chamber or an atrial chamber. For the remainder of the below discussion, unless stated otherwise, it is assumed that the LP that performs step 501, as well as other steps shown on the left in FIG. 5A (and FIGS. 5B and 5C), are performed by an LP (e.g., 102b) implanted in the right ventricular chamber.

Referring again to FIG. 5A, step 511 involves the LP determining cardiac activity information based on the NF-EGM sensed by the LP and optionally and likely also based on paced cardiac events caused by the LP performing pacing. As part of step 511, the LP can, for example, detect R-waves indicative of ventricular depolarizations based on the NF-EGM, and/or detect P-waves indicative of atrial depolarization based on the NF-EGM, by comparing the NF-EGM, or samples thereof, to a corresponding R-wave threshold and/or P-wave threshold, as is known in the art. Additionally, or alternatively, an R-wave morphology template can be used to detect R-waves and/or a P-wave morphology template can be used to detect P-waves. These are just a few examples of how an LP can detect cardiac activity information based on a NF-EGM, which are not intended to be all-encompassing. For the remainder of the below discussion, unless stated otherwise, it is presumed that the LP detects R-wave based on the NF-EGM. Based on the detected R-waves, and/or based on pacing pulses delivered by the LP, the LP can determine a heart rate and/or beat-to-beat interval associated with each cardiac event sensed and paced by the LP, and based on the sensed and paced cardiac events the LP can determine the cardiac activity information.

Examples of the cardiac activity information that the LP determines include, but are not limited to: a rate metric indicative of heart rate (HR), an interval metric indicative of beat-to-beat interval (e.g., R-R interval), an indicator of whether the rate metric indicative of HR exceeds a corresponding rate metric threshold, an indicator of whether the rate metric indicative of HR is within a corresponding rate metric range, an indicator of whether the interval metric indicative of beat-to-beat interval is below a corresponding interval metric threshold, an indicator of whether the interval metric indicative of beat-to-beat interval is within a corresponding interval metric range, an indicator that a sensed cardiac event occurred and/or an indicator that a paced cardiac event occurred. The rate metric indicative of heart rate can be a running average HR, a median HR, or an instantaneous HR, but is not limited thereto. The interval metric indicative of beat-to-beat interval can be a running average beat-to-beat interval, a median beat-to-beat interval, or an instantaneous beat-to-beat interval, but is not limited thereto. Each of an indicator of whether a rate metric indicative of heart rate has exceeded a rate threshold, an indicator of whether the rate metric indicative of heart rate is within a corresponding rate range, an indicator of whether an interval metric indicative of beat-to-beat interval is below an interval threshold, or an indicator of whether the interval metric indicative of beat-to-beat interval is within a corresponding interval range, can comprises, e.g., one or more flags, bits, bytes, or the like, that is/are included in a header or payload of one or more i2i messages. Other variations are also possible and within the scope of the embodiments described herein. Each of the aforementioned running averages (which are also known as moving averages) can be a simple unweighted running average, a weighted running average, or an exponential running average, but is not limited thereto. Additional and/or alternative types of cardiac activity information that can be determined by the LP, sent (transmitted) from the LP to the NV-ICD, and used by the NV-ICD to detect an arrhythmic episode and/or perform arrhythmia discrimination. Examples of such additional and/or alternative types of cardiac activity information include information related to a morphology of an NF-EGM sensed by the LP, such as, but not limited to, morphological information related to QRS complexes, P-waves, and/or other morphological features of the NF-EGM sensed by the LP. The LP itself can determine whether such morphological features (e.g., QRS complexes) are normal complexes or non-normal complexes and can provide such indications to the NV-ICD. In certain such embodiments, the LP can determine whether such morphological features (e.g., QRS complexes) are classified as a VT complex, a VF complex, etc. The LP can use morphology template matching, wavelet decomposition, and/or the like, to make such determinations. This type of morphological cardiac activity information, that the LP can provide to the NV-ICD, could be useful to the NV-ICD when monitoring for an arrhythmic episode and/or performing arrhythmia discrimination, especially where the NV-ICD is unable to determine such morphological cardiac activity information itself from the FF-EGM sensed by the NV-ICD.

Referring again to FIG. 5A, step 521 involves the LP monitoring for one or more specific pacemaker conditions, and step 531 involves the LP determining whether at least one of the one or more specific pacemaker conditions was detected. If the answer to the determination at step 531 is No, then flow returns to step 501. If the answer to the determination at step 531 is Yes, then flow goes to step 541. As will be described in additional detail below, with reference to FIG. 5B, a specific pacemaker condition that the LP can monitor for at step 521 is whether the LP received a request from the NV-ICD for the LP to sent cardiac activity information to the NV-ICD. Another example of a specific cardiac condition that the LP can monitor for at step 521 relates to the LP detecting a specific cardiac condition, such as a rate metric exceeding a corresponding rate metric threshold, or an interval metric falling below a corresponding interval metric threshold. Other variations are also possible, and are within the scope of the embodiments described herein, as would be understood by one of skill in the art reading this description.

Still referring to FIG. 5A, step 541 involves the LP sending one or more i2i messages including the cardiac activity information to the NV-ICD. Such i2i messages can be sent as conductive communication signals transmitted through patient tissue using electrodes (e.g., 108a, 108b) of the LP. Alternatively, if the LP includes an antenna and is capable of performing RF communication, the i2i messages can be sent as RF signals. Depending on how much cardiac activity information is sent, the specific protocol used, and the specific type of communication technology used, the cardiac activity information can be sent in a single i2i message or multiple i2i messages.

Step 550 involves the NV-ICD receiving the one or more i2i messages, including the cardiac activity information, from the LP. Where the i2i messages sent by the LP at step 541 are sent as conductive communication signals, the NV-ICD can use electrodes (e.g., 422) and a conductive communication receiver (e.g., 420) to receive the i2i messages. Where the i2i messages sent by the LP at step 541 are sent as RF communication signals, the NV-ICD can use an antenna (e.g., 415) of an RF receiver (e.g., which can be part of the RF telemetry circuit 414) to receive the i2i messages.

Step 560 involves the NV-ICD, based on the cardiac activity information obtained from the LP via at least one of the one or more of the i2i messages received by the NV-ICD from the LP, monitoring for an arrhythmic episode and/or performing arrhythmia discrimination. Arrhythmia discrimination, as the term is used herein, refers to one or more of classifying a detected arrhythmic episode as a specific type of arrhythmia (e.g., classifying a detected tachyarrhythmia episode as either VT, AF, or VF), determining whether a detected arrhythmic episode has been misclassified, or determining whether a detected arrhythmic episode was a false positive detection (e.g., a VT detection was a false positive VT detection). Where step 560 results in the NV-ICD detecting for a specific type of arrhythmic episode, the NV-ICD can deliver therapy to attempt to terminate the arrhythmic episode and/or send one or more i2i messages to the LP that instructs the LP to perform therapy to attempt to terminate the arrhythmic episode.

Figure 5B:
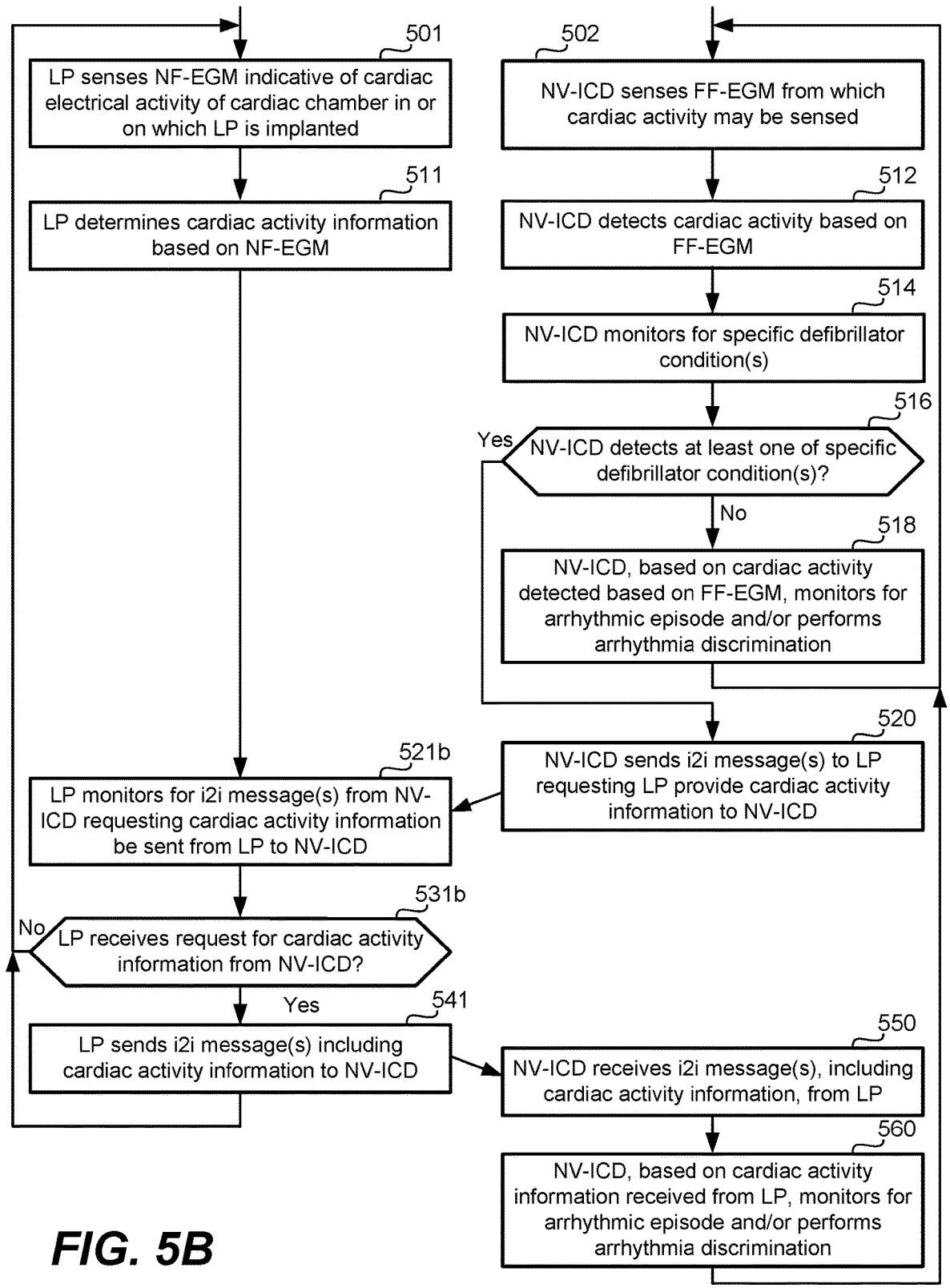
FIG. 5B is a high level flow diagram that is used to describe certain embodiments of the present technology wherein an LP sends cardiac activity information to an NV-ICD, in response to the NV-ICD sending a request for such information to the LP.

The high level flow diagram of FIG. 5B will now be used to describe embodiments where the LP provides supplemental information, and more specifically cardiac activity information, to the NV-ICD in response to receiving an on-demand request from the NV-ICD. Some of the steps in FIG. 5B are the same as those described above with reference to FIG. 5A, in which cases, the steps are numbered the same in FIG. 5B as they were in FIG. 5A, and need not be described again in detail. As was also the cased in FIG. 5A, the steps shown on the left are performed by the LP (e.g., 102b) and the steps shown on the right are performed by the NV-ICD (e.g., 106).

Referring to FIG. 5B, step 501 involves the LP sensing a NF-EGM indicative of cardiac electrical activity of a cardiac chamber in or on which the LP is implanted. Since step 501 in FIG. 5B is the same as step 501 in FIG. 5A, additional details of step 501 can be appreciated from the above discussion of FIG. 5A, and need not be described again. Step 511 involves the LP determining cardiac activity information based on the NF-EGM sensed by the LP and optionally and likely also based on paced cardiac events caused by the LP performing pacing. Since step 511 in FIG. 5B is the same as step 511 in FIG. additional details of step 511 can be appreciated from the above discussion of FIG. and need not be described again.

Still referring to FIG. 5B, as shown on the right, at step 502 the NV-ICD senses a far-field EGM (FF-EGM) from which cardiac activity may be detected. Referring briefly back to FIG. 4, the FF-EGM can, for example, be sensed using extracardiac electrodes (e.g., 422) and a sensing amplifier (e.g., 408). At step 512 the NV-ICD detects cardiac events from the FF-EGM. The cardiac events that the NV-ICD detects can be, e.g., sensed or paced cardiac events, and in specific embodiments, sensed or paced ventricular depolarizations. The NV-ICD can, for example, use one or more thresholds (e.g., an R-wave threshold) and/or one or more morphological templates (e.g., an R-wave template) to detect cardiac events, but is not limited thereto.

Still referring to FIG. 5B, at step 514 the NV-ICD monitors for one or more specific defibrillator conditions, which in certain embodiments as explained in more detail below, can be conditions that if detected indicates that the NV-ICD should not trust the cardiac activity detected from the FF-EGM. At step 516 the NV-ICD determines whether at least one of the one or more specific defibrillator conditions is detected. If the answer to the determination at step 516 is No, then flow goes to step 518. If the answer to the determination at step 516 is Yes, then flow goes to step 520.

If flow makes it to step 518, then at step 518 the NV-ICD monitors for an arrhythmic episode and/or performs arrhythmia discrimination based on cardiac activity that the NV-ICD detected based on the FF-EGM sensed by the NV-ICD.

However, if instead flow goes to step 520, then the NV-ICD sends one or more i2i messages to the LP requesting that the LP provide cardiac activity information to the NV-ICD. In certain embodiments, the i2i message(s) that the NV-ICD sends to the LP is sent using conductive communication. In other embodiments, the i2i message(s) that the NV-ICD sends to the LP is sent using RF communication.

An example defibrillator condition, that the NV-ICD may monitor for at step 514, is that cardiac activity detected by the NV-ICD from the FF-EGM is likely being at least one of under-sensed or over-sensed. Any one or more known or future developed under-sensing and/or over-sensing algorithms can be used to determine whether such a defibrillator condition is detected. Another defibrillator condition that the NV-ICD may monitor for at step 514, is that cardiac activity detected from the FF-EGM is likely not accurate due to an extracardiac signal. Any one or more known or future developed noise detections algorithms can be used be used, for example, to determine whether cardiac activity detected from the FF-EGM is likely not accurate due to an extracardiac signal. The extracardiac signal can be, for example, an electromagnetic interference (EMI) signal, an electromyogenic signal, noise that occurs due to insulation on a lead failing or some other lead or electrode related failure, but is not limited thereto. These are just a few examples of the types of defibrillator conditions that the NV-ICD may monitor for at step 514. The NV-ICD can monitor for additional and/or alternative defibrillator condition(s) at step 514, wherein if the condition is detected, the NV-ICD knows that it should not trust the cardiac activity detected from the FF-EGM, and thus, should request cardiac activity information from the LP.

At noted above, at step 520 the NV-ICD sends one or more i2i messages to the LP requesting that the LP provide cardiac activity information (determined by the LP) to the NV-ICD. As shown in FIG. 5B, at step 521b the LP monitors for i2i message(s) from the NV-ICD, wherein such a message may be a request from the NV-ICD for the LP to send cardiac activity information (determined by the LP) to the NV-ICD. At step 531b the LP determines whether it has received a request for cardiac activity information from the NV-ICD. If the answer to the determination at step 531b is No, then flow returns to step 501. If the answer to the determination at step 531b is Yes, then flow goes to step 541. Step 521b is a specific implementation of step 521 discussed above with reference to FIG. 5A, and step 531b is a specific implementation of step 531 discussed above with reference to FIG. 5A.

Still referring to FIG. 5B, step 541 involves the LP sending one or more i2i messages including the cardiac activity information to the NV-ICD. Since step 541 in FIG. 5B is the same as step 541 in FIG. 5A, additional details of step 541 can be appreciated from the above discussion of FIG. 5A, and need not be described again.

Still referring to FIG. 5B, step 550 involves the NV-ICD receiving the one or more i2i messages, including the cardiac activity information, from the LP. Since step 550 in FIG. 5B is the same as step 550 in FIG. 5B, additional details of step 550 can be appreciated from the above discussion of FIG. 5A, and need not be described again. Step 560 then involves the NV-ICD, based on the cardiac activity information obtained from the LP via at least one of the one or more of the i2i messages received by the NV-ICD from the LP, monitoring for an arrhythmic episode and/or performing arrhythmia discrimination. Since step 560 in FIG. 5B is the same as step 560 in FIG. 5A, additional details of step 560 can be appreciated from the above discussion of FIG. 5A, and need not be described again.

In still another embodiment, the NV-ICD can detect an arrhythmic episode based on the FF-EGM sensed by the NV-ICD, and in response thereto the NV-ICD can send one or more i2i messages to the LP requesting that the LP send cardiac activity information (determined by the LP) to the NV-ICD. In other words, another example of defibrillator condition monitored for at step 514 can be an arrhythmic episode. The NV-ICD can then, after received the cardiac activity information from the LP, perform arrhythmia discrimination to classify the arrhythmic episode that had been originally detected by the NV-ICD. The NV-ICD may additionally, or alternatively, use cardiac activity information that the NV-ICD receives from the LP to determine whether or not the arrhythmic episode originally detected by the NV-ICD was a false positive or a true positive detection.

The above described embodiments are examples of embodiments where the NV-ICD selectively sends one or more i2i messages to the LP requesting that the LP provide cardiac activity information to the NV-ICD, based upon which the NV-ICD can monitor for an arrhythmic episode and/or perform arrhythmia discrimination. In other words, the above described embodiments are examples of embodiments where the NV-ICD sends on-demand requests to the LP, and the LP responds thereto. Other variations are also possible and within the scope of the embodiments described herein.

Figure 5C:
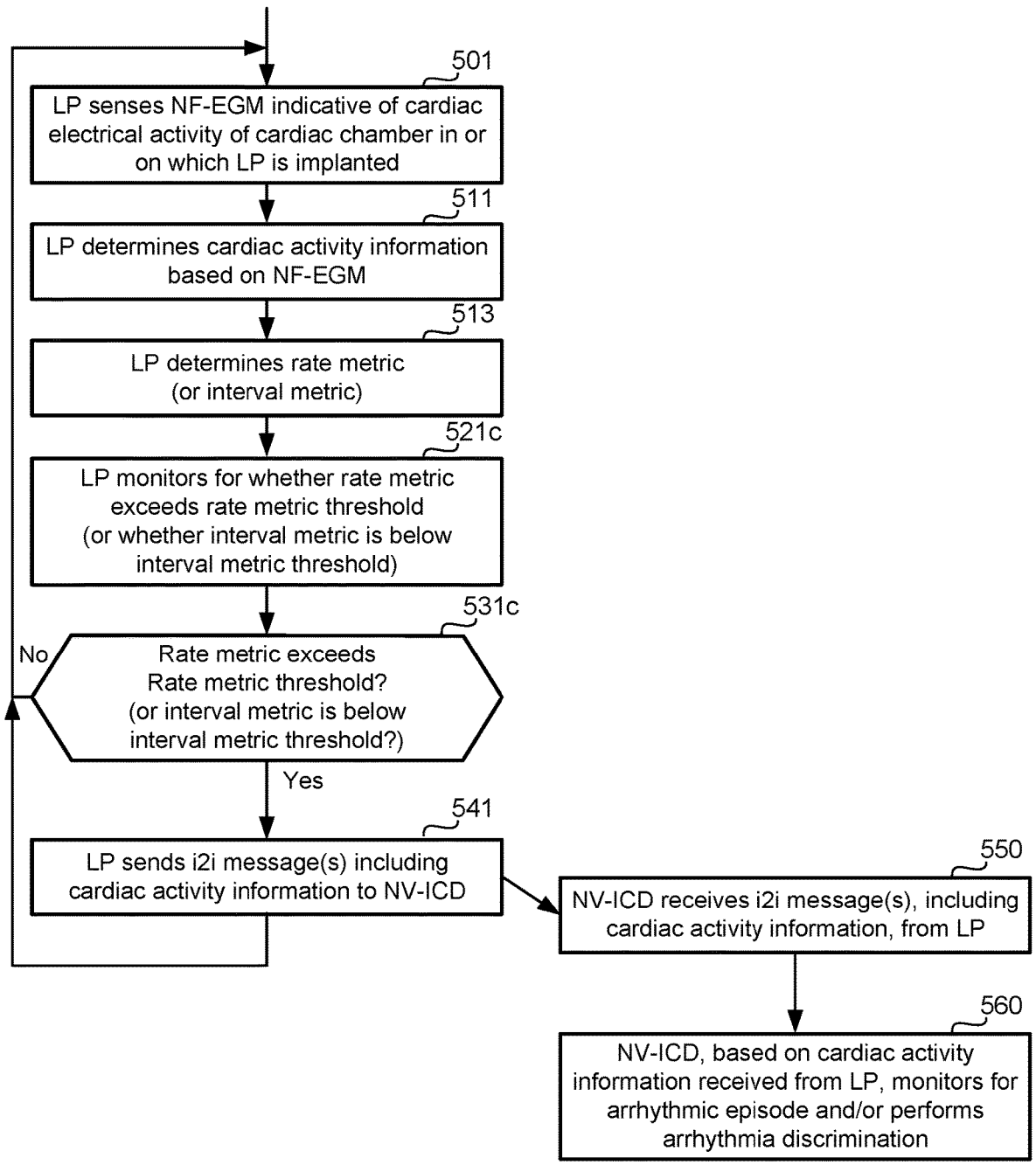
FIG. 5C is a high level flow diagram that is used to describe certain embodiments of the present technology wherein an LP sends cardiac activity information to an NV-ICD, without receiving any request for such information from the NV-ICD.

The high level flow diagram of FIG. 5C will now be used to describe embodiments where the LP provides on-demand transmissions of cardiac activity information to an NV-ICD when deemed necessary or appropriate by the LP, without receiving requests from the NV-ICD. Some of the steps in FIG. 5C are the same as those described above with reference to FIG. 5A, in which cases, the steps are numbered the same in FIG. 5C as they were in FIG. 5A, and need not be described again in detail. As was also the case in FIGS. 5A and 5B, the steps shown on the left are performed by the LP (e.g., 102b) and the steps shown on the right are performed by the NV-ICD (e.g., 106).

Referring to FIG. 5C, step 501 involves the LP sensing a NF-EGM indicative of cardiac electrical activity of a cardiac chamber in or on which the LP is implanted. Since step 501 in FIG. 5C is the same as step 501 in FIG. 5A, additional details of step 501 can be appreciated from the above discussion of FIG. 5A, and need not be described again. Step 511 involves the LP determining cardiac activity information based on the NF-EGM sensed by the LP and optionally and likely also based on paced cardiac events caused by the LP performing pacing. Since step 511 in FIG. 5C is the same as step 511 in FIG. additional details of step 511 can be appreciated from the above discussion of FIG. and need not be described again.

Still referring to FIG. 5C, step 513 involves the LP determining a rate metric indicative of the patient's HR, or an interval metric indicative of the patient's B-B interval. The rate metric can be, for example, a present HR for the most recently detected beat, a running average of a predetermined number (e.g., 8) of most recent beats, or a median of a predetermined number (e.g., 8) of most recent beats, but is not limited thereto. The interval metric can be a present B-B interval, which can be the interval between a present R-wave and an immediately preceding R-wave, i.e., can be a most recent R-R interval. The present B-B interval, can alternatively be the interval between a present P-wave and an immediately preceding P-wave, i.e., can be a most recent P-P interval. The interval metric can alternatively be a running average of a predetermined number of most recent R-R intervals, or a median of a predetermined number of most recent R-R intervals. In still other embodiments, the interval metric can be a running average of a predetermined number of most recent P-P intervals, or a median of a predetermined number of most recent P-P intervals. Other variations are also possible and within the scope of the embodiments described herein.

At step 521c, which is a specific implementation of step 521 introduced above in FIG. 5A, the LP monitors for whether the rate metric exceeds a specified rate metric threshold, or whether the interval metric is below a specified interval metric threshold. The rate metric threshold can be a ventricular tachycardia (VT) threshold. Alternatively, or additionally, the rate metric threshold can be a ventricular fibrillation (VF) threshold. An example of a VT threshold, which could be used as the rate metric threshold, is 200 beats per minute (bpm), but is not limited thereto. An example of a VF threshold, which could be used as the rate metric threshold, is 300 bpm, but is not limited thereto. Similarly, the interval metric threshold(s) can correspond to VT and/or VF. An example VT threshold, that could be used as the interval metric threshold is 300 milliseconds, but is not limited thereto. An example VF threshold, that could be used as the interval metric threshold is 200 milliseconds, but is not limited thereto.

At step 531c, which is a specific implementation of step 531 introduced above in FIG. 5A, the LP determines whether the rate metric exceeds a specified rate metric threshold, or whether the interval metric is below a specified interval metric threshold. If the answer to the determination at step 531c is No, then flow goes back to step 501. If the answer to the determination at step 531c is Yes, then flow goes to step 541. While steps 521c and 531c were shown and described at two separate steps, these steps can equivalently be combined into a single step.

Step 541 involves the LP sending one or more i2i messages including the cardiac activity information to the NV-ICD. Since step 541 in FIG. 5C is the same as step 541 in FIG. 5A, additional details of step 541 can be appreciated from the above discussion of FIG. 5A, and need not be described again.

Step 550 involves the NV-ICD receiving the one or more i2i messages, including the cardiac activity information, from the LP. Step 560 involves the NV-ICD, based on the cardiac activity information obtained from the LP via at least one of the one or more of the i2i messages received by the NV-ICD from the LP, monitoring for an arrhythmic episode and/or performing arrhythmia discrimination. Examples of the cardiac information that can be sent by the LP to the NV-ICD were described above. Additional details of step 550 and 560 can be appreciated from the above discussion of FIG. 5A, and need not be described again.

In a variation of the embodiment summarized above with reference to FIG. 5C, when the answer to the determination at step 531c is Yes, the LP sends one or more i2i messages including cardiac activity information to the NV-ICD once every Mth paced/sensed event, where 1≤M; and when the answer to the determination at step 531c is No, the LP sends one or more i2i messages including cardiac activity information to the NV-ICD once every Nth paced/sensed event, where N>M. In other words, in such an embodiment, the frequency at which the LP sends cardiac activity information to the NV-ICD is greater when the rate metric exceeds the rate metric threshold (or the interval metric is below the interval metric threshold). For a more specific example, where N=1 and M=4, when the rate metric exceeds the rate metric threshold (or the interval metric is below the interval metric threshold) the LP sends cardiac activity information to the NV-ICD once every paced/sensed event (i.e., once every heart beat), and when the rate metric does not exceed the rate metric threshold (or the interval metric is not below the interval metric threshold) the LP sends cardiac activity information to the NV-ICD every fourth paced/sensed event (i.e., once every four heart beats).

In other words, the frequency at which the LP transmits cardiac information to the NV-ICD can depend on a rate metric or an interval metric determined by the LP. For example, the LP can determine a rate metric indicative of heart rate (or an interval metric indicative of R-R interval or P-P interval), based on the NF-EGM sensed by the LP. The LP can then determine when the rate metric exceeds a corresponding rate metric threshold (or the interval metric is below a corresponding interval metric threshold), and in response thereto, the LP sends at least one i2i message including cardiac activity information to the NV-ICD each time the LP senses an intrinsic cardiac depolarization and each time the LP delivers a pacing pulse, while the rate metric continues to exceed the corresponding rate metric threshold or the interval metric continues to be below the corresponding interval metric threshold. The LP can then stop sending cardiac activity information to the NV-ICD, when the rate metric no longer exceeds the corresponding rate metric threshold (or the interval metric is no longer below the corresponding interval metric threshold). Alternatively, rather than the LP completely stop sending cardiac activity information to the NV-ICD, it can reduce the frequency of sending the cardiac activity information to the NV-ICD. In other words, the LP sends at least one i2i message including cardiac activity information to the NV-ICD, less frequently than each time the LP senses an intrinsic cardiac depolarization or delivers a pacing pulse, when the rate metric does not exceed the corresponding rate metric threshold or the interval metric is not below the corresponding interval metric threshold.

In certain other embodiments, the LP sends an i2i message including cardiac activity information to the NV-ICD each time the LP senses an intrinsic cardiac depolarization and each time the LP delivers a pacing pulse, regardless of whether any specific condition is detected. In other words, the LP informs the NV-ICD of each cardiac event sensed by the LP and each cardiac event paced by the LP.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable system, comprising:
a leadless pacemaker (LP) comprising two or more electrodes and configured to be implanted in or on a cardiac chamber of a heart, the LP configured to use at least two of the two or more electrodes to sense a near-field electrogram (NF-EGM) and to selectively pace the cardiac chamber; and
a non-vascular implantable cardioverter defibrillator (NV-ICD) comprising two or more extracardiac electrodes configured to be implanted external to the heart, the NV-ICD configured to use at least two of the two or more extracardiac electrodes to sense a far-field electrogram (FF-EGM), and the NV-ICD configured to use at least two of the two or more extracardiac electrodes to selectively deliver a defibrillation shock to the heart;
the LP comprising a transmitter configured to selectively send implant-to-implant (i2i) messages to the NV-ICD and a receiver configured to receive i2i messages from the NV ICD; and
the NV-ICD comprising a receiver configured to receive the i2i messages from the LP and a transmitter configured to selectively send i2i messages to the LP;
wherein the NV-ICD is configured to
normally monitor for an arrhythmic episode and perform arrhythmia discrimination based on cardiac activity detected by the NV-ICD itself from the FF-EGM sensed by the NV-ICD, without using cardiac activity information obtained from the LP;
determine itself when the cardiac activity detected by the NV-ICD itself from the FF-EGM is likely being at least one of under-sensed or over-sensed, and in response thereto, send one or more i2i messages to the LP requesting that the LP provide cardiac activity information to the NV-ICD, based upon which the NV-ICD can at least one of monitor for an arrhythmic episode or perform arrhythmia discrimination; and
at least one of monitor for an arrhythmic episode or perform arrhythmia discrimination based on cardiac activity information obtained from the LP via one or more i2i messages received from the LP, following the NV-ICD sending the one or more i2i messages to the LP requesting that the LP provide cardiac activity information to the NV-ICD; and
wherein the LP is configured to
determine cardiac activity information based on sensed cardiac events detected from the NF-EGM and optionally also based on paced cardiac events caused by the LP performing pacing;
monitor for one or more specific pacemaker conditions, wherein one of the one or more specific pacemaker conditions that the LP is configured to monitor for, and in response to which being detected the LP sends one or more i2i messages including the cardiac activity information to the NV-ICD, comprises the LP receiving at least one of the one or more i2i messages from the NV-ICD requesting that the LP provide cardiac activity information to the NV-ICD;
send one or more i2i messages including the cardiac activity information to the NV-ICD in response to receiving at least one of the one or more i2i messages from the NV-ICD requesting that the LP provide cardiac activity information to the NV-ICD; and
not send one or more i2i messages including the cardiac activity information to the NV-ICD when none of the one or more specific pacemaker conditions is detected by the LP.

2. The implantable system of claim 1, wherein:
the NV-ICD is further configured to determine itself when an extracardiac signal is likely preventing the NV-ICD from accurately detecting cardiac activity based on the FF-EGM sensed by the NV-ICD, and in response thereto, send one or more i2i messages to the LP requesting that the LP provide cardiac activity information to the NV-ICD, based upon which the NV-ICD can at least one of monitor for an arrhythmic episode or perform arrhythmia discrimination.

3. The implantable system of claim 1, wherein:
the LP is configured to continue sending the one or more i2i messages including cardiac activity information to the NV-ICD when at least one of the one or more specific pacemaker conditions continues to be detected; and
the LP is configured to stop sending the one or more i2i messages including cardiac activity information to the NV-ICD when none of the one or more specific pacemaker conditions continues to be detected.

4. The implantable system of claim 1, wherein the LP is configured to:
determine a rate metric indicative of heart rate or an interval metric indicative of beat-to-beat interval, based on the NF-EGM sensed by the LP;

determine when the rate metric exceeds a corresponding rate metric threshold or the interval metric is below a corresponding interval metric threshold; and send the one or more i2i messages including cardiac activity information to the NV-ICD, less frequently than each time the LP senses an intrinsic cardiac depolarization or delivers a pacing pulse, when a rate metric does not exceed a corresponding rate metric threshold or an interval metric is not below a corresponding interval metric threshold.

5. The implantable system of claim 1, wherein the cardiac activity information determined by the LP and included in the one or more i2i messages the LP sends to the NV-ICD comprises at least one of the following:

a rate metric indicative of heart rate;

an interval metric indicative of beat-to-beat interval;

an indicator of whether the rate metric indicative of heart rate exceeds a corresponding rate metric threshold;

an indicator of whether the rate metric indicative of heart rate is within a corresponding rate metric range;

an indicator of whether the interval metric indicative of beat-to-beat interval is below a corresponding interval metric threshold;

an indicator of whether the interval metric indicative of beat-to-beat interval is within a corresponding interval metric range;

an indicator that a sensed cardiac event occurred;

an indicator that a paced cardiac event occurred; or information related to morphology of the NF-EGM sensed by the LP.

6. The implantable system of claim 1, wherein the LP is configured to be implanted in or on a ventricular chamber of the heart, or to be implanted in or on an atrial chamber of the heart.

7. The implantable system of claim 1, wherein the LP is configured to be implanted in or on a first cardiac chamber of the heart, and the implantable system comprises a further LP configured to implanted in or on a second cardiac chamber of the heart.

8. A method for use by an implantable system including a leadless pacemaker (LP) and a non-vascular implantable cardioverter defibrillator (NV-ICD), the method comprising:

the NV-ICD sensing a far-field electrogram (FF-EGM);

the LP sensing a near-field electrogram (NF-EGM) indicative of cardiac electrical activity of a cardiac chamber in or on which the LP is implanted;

the LP determining cardiac activity information based on the NF-EGM sensed by the LP and optionally also based on paced cardiac events caused by the LP performing pacing;

the NV-ICD normally monitoring for an arrhythmic episode or performing arrhythmia discrimination based on cardiac activity detected by the NV-ICD itself from the FF-EGM sensed by the NV-ICD, without using cardiac activity information obtained from the LP;

the NV-ICD determining itself when the cardiac activity detected by the NV-ICD itself from the FF-EGM is likely being at least one of under-sensed or over-sensed, and in response thereto, sending one or more i2i messages to the LP requesting that the LP provide cardiac activity information to the NV-ICD, based upon which the NV-ICD can at least one of monitor for an arrhythmic episode or perform arrhythmia discrimination;

the NV-ICD at least one of monitoring for an arrhythmic episode or performing arrhythmia discrimination based on cardiac activity information obtained from the LP via one or more i2i messages received from the LP, following the NV-ICD sending the one or more i2i messages to the LP requesting that the LP provide cardiac activity information to the NV-ICD; and the LP monitoring for one or more specific pacemaker conditions, wherein one of the one or more specific pacemaker conditions that the LP monitors for, and in response to which being detected the LP sends one or more i2i messages including the cardiac activity information to the NV-ICD, comprises the LP receiving at least one of the one or more i2i messages from the NV-ICD requesting that the LP provide cardiac activity information to the NV-ICD;

the LP transmitting one or more i2i messages including the cardiac activity information to the NV-ICD in response to the LP receiving at least one of the one or more i2i messages from the NV-ICD requesting that the LP provide cardiac activity information to the NV-ICD; and the LP not transmitting one or more i2i messages including the cardiac activity information to the NV-ICD when none of the one or more specific pacemaker conditions is detected by the LP.

9. The method of claim 8, further comprising:

the NV-ICD determining itself that an extracardiac signal is likely preventing the NV-ICD from accurately detecting cardiac activity based on the FF-EGM sensed by the NV-ICD, and in response thereto, the NV-ICD sending one or more i2i messages to the LP requesting that the LP provide cardiac activity information to the NV-ICD, based upon which the NV-ICD can at least one of monitor for an arrhythmic episode or perform arrhythmia discrimination.

10. The method of claim 8, further comprising:

the LP continuing sending the one or more i2i messages including cardiac activity information to the NV-ICD when at least one of the one or more specific pacemaker conditions continues to be detected; and the LP stopping sending the one or more i2i messages including cardiac activity information to the NV-ICD when none of the one or more specific pacemaker conditions continues to be detected.

11. The method of claim 8, further comprising:

the LP determining a rate metric indicative of heart rate or an interval metric indicative of beat-to-beat interval, based on the NF-EGM sensed by the LP;

the LP determining when the rate metric exceeds a corresponding rate metric threshold or the interval metric is below a corresponding interval metric threshold; and the LP sending the one or more i2i messages including cardiac activity information to the NV-ICD, less frequently than each time the LP senses an intrinsic cardiac depolarization or delivers a pacing pulse, when the rate metric does not exceed a corresponding rate metric threshold or the interval metric is not below a corresponding interval metric threshold.

12. The method of claim 8, wherein the cardiac activity information determined by the LP and included in the one or more i2i messages the LP sends to the NV-ICD comprises at least one of the following:

a rate metric indicative of heart rate;

an interval metric indicative of beat-to-beat interval;

an indicator of whether the rate metric indicative of heart rate exceeds a corresponding rate metric threshold;

an indicator of whether the rate metric indicative of heart rate is within a corresponding rate metric range;

an indicator of whether the interval metric indicative of beat-to-beat interval is below a corresponding interval metric threshold;
an indicator of whether the interval metric indicative of beat-to-beat interval is within a corresponding interval metric range;
an indicator that a sensed cardiac event occurred;
an indicator that a paced cardiac event occurred; or
information related to morphology of the NF-EGM sensed by the LP.

13. The method of claim 8, wherein the LP is configured to be implanted in or on a ventricular chamber of a heart, or to be implanted in or on an atrial chamber of the heart.

14. The method of claim 8, wherein the LP is configured to be implanted in or on a first cardiac chamber of a heart, and the implantable system comprising a further LP configured to implanted in or on a second cardiac chamber of the heart.

\* \* \* \* \*